United States Patent
Dou

(10) Patent No.: US 11,560,575 B2
(45) Date of Patent: Jan. 24, 2023

(54) HIGH EFFICIENT DELIVERY OF PLASMID DNA INTO HUMAN AND VERTEBRATE PRIMARY CELLS IN VITRO AND IN VIVO BY NANOCOMPLEXES

(71) Applicant: Texas Tech University System, Lubbock, TX (US)

(72) Inventor: Huanyu Dou, El Paso, TX (US)

(73) Assignee: Texas Tech University System, Lubbock, TX (US)

(*) Notice: Subject to any disclaimer, the term of this patent is extended or adjusted under 35 U.S.C. 154(b) by 316 days.

(21) Appl. No.: 16/956,627

(22) PCT Filed: Dec. 3, 2018

(86) PCT No.: PCT/US2018/063546
§ 371 (c)(1),
(2) Date: Jun. 22, 2020

(87) PCT Pub. No.: WO2019/133190
PCT Pub. Date: Jul. 4, 2019

(65) Prior Publication Data
US 2021/0095309 A1    Apr. 1, 2021

Related U.S. Application Data

(60) Provisional application No. 62/611,673, filed on Dec. 29, 2017.

(51) Int. Cl.
*C07H 21/02* (2006.01)
*C07H 21/04* (2006.01)
*C12N 15/85* (2006.01)
*C12N 15/113* (2010.01)
*C12N 15/88* (2006.01)

(52) U.S. Cl.
CPC ............ *C12N 15/85* (2013.01); *C12N 15/113* (2013.01); *C12N 15/88* (2013.01)

(58) Field of Classification Search
CPC .................................................... C12N 15/113
See application file for complete search history.

(56) References Cited

FOREIGN PATENT DOCUMENTS

WO    2017/100744 A1    6/2017
WO    2017/201076 A1    11/2017

OTHER PUBLICATIONS

Pollard, J. W. "Trophic macrophages in development and disease." Nat Rev Immunol 9, 259-270, doi:10.1038/nri2528 (2009).
Rapti, K. et al. "Targeted Gene Therapy for the Treatment of Heart Failure." Can J Cardiol 27, 265-283, doi:10.1016/j.cjca.2011.02.005 (2011).
Rigamonti, E. et al. "Plasticity in Skeletal Muscle Repair." BioMed research international, doi:Artn 560629.
Rojanasakul, Y. et al. "The Transport Barrier of Epithelia—a Comparative-Study on Membrane-Permeability and Charge Selectivity in the Rabbit." Pharmaceutical research 9, 1029-1034, doi:Doi 10.1023/A:1015802427428 (1992).
Shaw, P. J. et al. "The nucleolus." Annu Rev Cell Dev Bi 11, 93-121, doi:DOI10.1146/annurev.cellbio.11.1.93 (1995).
Shukla, S. K. et al. "Cytotoxic and radioprotective effects of Podophyllum hexandrum." Environmental toxicology and pharmacology 22, 113-120, doi:10.1016/j.etap.2006.01.001 (2006).
Sica, A. et al. "Macrophage plasticity and polarization: in vivo veritas." The Journal of clinical investigation 122, 787-795, doi:10.1172/JCI59643 (2012).
Stempin, C. C. et al. "Arginase in Parasitic Infections: Macrophage Activation, Immunosuppression, and Intracellular Signals." J Biomed Biotechnol, doi:Artn 683485 10.1155/2010/683485 (2010).
Sun, T.-M. et al. "Simultaneous Delivery of siRNA and Paclitaxel via a "Two-in-One" Micelleplex Promotes Synergistic Tumor Suppression." ACS Nano 5, 1483-1494, doi:10.1021/nn103349h (2011).
Von Harpe, A. et al. Characterization of commercially available and synthesized polyethylenimines for gene delivery. Journal of Controlled Release 69, 309-322, doi:Doi 10.1016/50168-3659(00)00317-5 (2000).
Vulliet, R. "Improved technique for the preparation of water-in-oil emulsions containing protein antigens." Biotechniques 20, 797-& (1996).
Wan, D. et al. "Can Nonspecific Host-Guest Interaction Lead to Highly Specific Encapsulation by a Supramolecular Nanocapsule?" Macromolecules 42, 6448-6456, doi:10.1021/ma900952e (2009).
Wan, D. et al. "Enhancing the unimolecularity and control for guest release of a macromolecular nanocapsule via core engineering." React. Funct. Polym. 70, 916-922, doi:http://dx.doi.org/10.1016/j.reactfunctpolym.2010.09.002 (2010).
Wang, Y. et al. "Co-delivery of drugs and DNA from cationic core-shell nanoparticles self-assembled from a biodegradable copolymer." Nat. Mater. 5, 791-796,doi:http://www.nature.com/nmat/journal/v5/n10/suppinfo/nmat1737_S1.html (2006).
Weecharangsan, W. et al. "Evaluation of chitosan salts as non-viral gene vectors in CHOK1 cells." International journal of pharmaceutics 348, 161-168, doi:10.1016/j.ijpharm.2007.07.011 (2008).
Wightman, L. et al. "Different behavior of branched and linear polyethylenimine for gene delivery in vitro and in vivo." The Journal of Gene Medicine 3, 362-372, doi:10.1002/jgm.187 (2001).

(Continued)

*Primary Examiner* — Amy H Bowman
(74) *Attorney, Agent, or Firm* — Edwin S. Flores; Daniel J. Chalker; Chalker Flores, LLP

(57) ABSTRACT

The present invention includes synthesis of polyethyleneimine800-EpoxyC8-22 (PEI800-C8-22) lipids, e.g., Polyethyleneimine800-EpoxyC16 (PEI800-C16), PEI12C16, PEI8C16, and PEI4C16 lipids, compositions and methods for transfecting primary leukocytes, myeloid cells, lymphoid cells, monocytes, macrophages and dendritic cells (DC) comprising a transfection complex comprising: one or more nanoparticles; and Polyethyleneimine800-EpoxyC16 (PEI800-C16), PEI12C16, PEI8C16, and PEI4C16 lipids complexed with one or more nucleic acids, such as, e.g., DNA, RNA, nucleic acid vectors, shRNA, miRNA, and RNAi on or about the nanoparticles.

20 Claims, 14 Drawing Sheets

(56) References Cited

OTHER PUBLICATIONS

Xiao, J. et al. "Low Molecular Weight Polyethylenimine-graft-Tween 85 for Effective Gene Delivery: Synthesis and in Vitro Characteristics." Bioconjugate Chem. 23, 222-231, doi:10.1021/bc200504v (2012).
Xie, J. et al., "A polyethylenimine-linoleic acid conjugate for antisense oligonucleotide delivery", BioMed Research International, 2013, pp. 1-7.
Xun, M.-M. et al. "Low molecular weight PEI-based polycationic gene vectors via Michael addition polymerization with improved serum-tolerance." Polymer 65, 45-54,doi:http://dx.doi.org/10.1016/j.polymer.2015.03.070 (2015).
Yamada, H. et al. "Design of Starch-graft-PEI Polymers: An Effective and Biodegradable Gene Delivery Platform." Biomacromolecules 15, 1753-1761, doi: 10.1021/bm500128k (2014).
Yao, H. et al. "Development of a Novel Low Toxicity and High Efficiency PEI-Based Nanopolymer for Gene Delivery In Vitro and In Vivo." Molecular Therapy 17, S64-S64 (2009).
Yin, H. et al. Non-viral vectors for gene-based therapy. Nat Rev Genet 15, 541-555, doi:10.1038/nrg3763 (2014).
Zhang, B. et al., "Cell-penetrating peptide-labelled smart polymers for enhanced gene delivery", Engineering in Life Sciences, 2017, vol. 17, No. 2, pp. 193-203.
Zhang, Q. F. et al. "Ring-opening polymerization for hyperbranched polycationic gene delivery vectors with excellent serum tolerance." ACS Appl Mater Interfaces 6, 15733-15742, doi:10.1021/am5046185 (2014).
Zhang, Y. H. et al. "Single-Molecule Study on Intermolecular Interaction between C-60 and Porphyrin Derivatives: Toward Understanding the Strength of the Multivalency." Langmuir : the ACS journal of surfaces and colloids 25, 6627-6632, doi:10.1021/la901360c (2009).
Zhi, D. et al. "The Headgroup Evolution of Cationic Lipids for Gene Delivery." Bioconjugate Chem. 24, 487-519, doi:10.1021/bc300381s (2013).
Zhu, J. et al. "Amphiphilic Core-Shell Nanoparticles with Poly(ethylenimine) Shells as Potential Gene Delivery Carriers." Bioconjugate Chem. 16, 139-146, doi:10.1021/bc049895l (2005).
Zintchenko, A. et al. "Simple modifications of branched PEI lead to highly efficient siRNA 5 carriers with low toxicity." Bioconjugate Chemistry 19, 1448-1455, doi:10.1021/bc800065f (2008).
Zou, L. et al. "Modification of side chain terminals of PEGylated molecular bottle brushes—A toolbar of molecular nanoobjects." Polymer 54, 481-484, doi:http://dx.doi.org/10.1016/j.polymer.2012.12.020 (2013).
Ando, M. et al. "Prevention of adverse events of interferon gamma gene therapy by gene delivery of interferon gamma-heparin-binding domain fusion protein in mice." Mol Ther-Meth Clin D 1, doi:Unsp 14023 10.1038/Mtm.2014.23 (2014).
Beyerle, A. et al. Toxicity Pathway Focused Gene Expression Profiling of PEI-Based Polymers for Pulmonary Applications. Molecular Pharmaceutics 7, 727-737, doi:10.1021/mp900278x (2010).
Bivas-Benita, M. et al. PLGA-PEI nanoparticles for gene delivery to pulmonary epithelium. European Journal of Pharmaceutics and Biopharmaceutics 58, 1-6, doi:10.1016/j.ejpb.2004.03.008 (2004).
Booth, C. et al. "Gene Therapy for Haemophagocytic Lymphohistiocytosis." Curr Gene Ther 14, 437-446 (2014).
Boussif, O. et al. "A versatile vector for gene and oligonucleotide transfer into cells in culture and in vivo polyethylenimine." Proc. Natl. Acad. Sci. USA 92, 7297-7301 (1995).
Cao, Q. et al. "Macrophages and Dendritic Cells for Treating Kidney Disease." Nephron Exp Nephrol 117, E47-E52, doi:10.1159/000320595 (2011).
Cassol, E. et al. "Macrophage polarization and HIV-1 infection." J Leukocyte Biol 87, 599-608, doi:10.1189/jlb.1009673 (2010).
Castanotto, D. et al. "The promises and pitfalls of RNA-interference-based therapeutics." Nature 457, 426-433, doi:10.1038/nature07758 (2009).

Chavez-Galan, L. et al. "Much more than M1 and M2 macrophages, there are also CD169(+) and TCR+ macrophages." Front Immunol 6, doi:Unsp 263 10.3389/Fimmu.2015.00263 (2015).
Chen, J. et al. "Charge-conversional zwitterionic copolymer as pH-sensitive shielding system for effective tumor treatment." Acta biomaterialia 26, 45-53, doi:10.1016/j.actbio.2015.08.018 (2015).
Chen, J. et al. "Polylysine-modified polyethylenimines as siRNA carriers for effective tumor treatment." Chinese J Polym Sci 33, 830-837, doi:10.1007/s10118-015-1632-0 (2015).
Choi, Y. S. et al. "Nanoparticles for gene delivery: therapeutic and toxic effects." Mol Cell Toxicol 10, 1-8, doi:10.1007/s13273-014-0001-3 (2014).
Chuang, C. C. et al. "Complexation of bioreducible cationic polymers with gold nanoparticles for improving stability in serum and application on nonviral gene delivery." ACS Appl Mater Interfaces 7, 7724-7731, doi:10.1021/acsami.5b00732 (2015).
Davis, M. E. et al. Evidence of RNAi in humans from systemically administered siRNA via targeted nanoparticles. Nature 464, 1067-U1140, doi:10.1038/nature08956 (2010).
Densmore, C. L. et al. "Aerosol delivery of robust polyethyleneimine-DNA complexes for gene therapy and genetic immunization." Mol Ther 1, 180-188, doi:10.1006/mthe.1999.0021 (2000).
Dizaj, S. M. et al. "A sight on the current nanoparticle-based gene delivery vectors." Nanoscale Res Lett 9, doi:Artn 252 10.1186/1556-276x-9-252 (2014).
Dong, W. et al. "Cross-linked Polyethylenimine as Potential DNA Vector for Gene Delivery with High Efficiency and Low Cytotoxicity." Acta Biochimica et Biophysica Sinica 38, 780-787, doi:10.1111/j.1745-7270.2006.00220.x (2006).
Dzik, J. M. "Evolutionary roots of arginase expression and regulation." Front Immunol 5, doi:Artn 544 10.3389/Fimmu.2014.00544 (2014).
Ferrante, C. J. et al. "Regulation of Macrophage Polarization and Wound Healing." Advances in wound care 1, 10-16, doi:10.1089/wound.2011.0307 (2012).
Fischer, D. et al. "In vitro cytotoxicity testing of polycations: influence of polymer structure on cell viability and hemolysis." Biomaterials 24, 1121-1131, doi:http://dx.doi.org/10.1016/S0142-9612(02)00445-3 (2003).
Flies, D. B. et al. "A simple and rapid vortex method for preparing antigen/adjuvant emulsions for immunization." J Immunol Methods 276, 239-242, doi:10.1016/S0022-1759(03)00081-4 (2003).
Forrest, M. L. et al. "A Degradable Polyethylenimine Derivative with Low Toxicity for Highly Efficient Gene Delivery." Bioconjugate Chemistry 14, 934-940, doi:10.1021/bc034014g (2003).
Freitas, S. et al. "Microencapsulation by solvent extraction/evaporation: reviewing the state of the art of microsphere preparation process technology." Journal of Controlled Release 102, 313-332, doi:10.1016/j.jconrel.2004.10.015 (2005).
Gao, D. et al. "Ultrasound-Triggered Phase-Transition Cationic Nanodroplets for Enhanced Gene Delivery." ACS Appl Mater Interfaces 7, 13524-13537, doi:10.1021/acsami.5b02832 (2015).
Gao, J.-Q. et al. "Gene-carried chitosan-linked-PEI induced high gene transfection efficiency with low toxicity and significant tumor-suppressive activity." International Journal of Pharmaceutics 387, 286-294, doi: 10.1016/j.jpharm.2009.12.033 (2010).
Gautam, A. et al. "Enhanced gene expression in mouse lung after PEI-DNA aerosol delivery." Mol Ther 2, 63-70, doi DOI 10.1006/mthe.2000.0087 (2000).
Gautam, A. et al. Pulmonary cytokine responses associated with PEI-DNA aerosol gene therapy. Gene Ther 8, 254-257, doi:DOI 10.1038/sj.gt.3301369 (2001).
Gautam, A. et al. "Transgene expression in mouse airway epithelium by aerosol gene therapy with PEI-DNA complexes." Mol Ther 3, 551-556, doi:10.1006/mthe.2001.0300 (2001).
Glass, C. K. et al. "Inflammation and Lipid Signaling in the Etiology of Insulin Resistance." Cell Metab 15, 635-645, doi:10.1016/j.cmet.2012.04.001 (2012).
Godbey, W. T. et al. "Poly(ethylenimine) and its role in gene delivery." Journal of Controlled Release 60, 149-160, doi:http://dx.doi.org/10.1016/S0168-3659(99)00090-5 (1999).
Gordon, S. "Alternative activation of macrophages." Nat Rev Immunol 3, 23-35, doi:10.1038/nri978 (2003).

(56) References Cited

OTHER PUBLICATIONS

Harush-Frenkel, O. et al. "Surface charge of nanoparticles determines their endocytic and transcytotic pathway in polarized MDCK cells." Biomacromolecules 9, 435-443, doi:10.1021/bm700535p (2008).

Kim, Y. H. et al. "Polyethylenimine with acid-labile linkages as a biodegradable gene carrier." Journal of Controlled Release 103, 209-219, doi:http://dx.doi.org/10.1016/j.jconrel.2004.11.008 (2005).

Kircheis, R. e al. Design and gene delivery activity of modified polyethylenimines. Adv Drug Deliver Rev 53, 341-358, doi:Doi 10.1016/S0169-409x(01)00202-2 (2001).

Lachelt, U. et al. "Nucleic Acid Therapeutics Using Polyplexes: A Journey of 50 Years (and Beyond)." Chem Rev 115, 11043-11078, doi:10.1021/cr5006793 (2015).

Lee, H. et al. "Molecularly self-assembled nucleic acid nanoparticles for targeted in vivo siRNA delivery." Nat Nanotechnol 7, 389-393, doi:10.1038/Nnano.2012.73 (2012).

Lee, Y. S. et al. "Bioreducible polymers for therapeutic gene delivery." Journal of Controlled Release 190, 424-439, doi:10.1016/j.jconrel.2014.04.012 (2014).

Liu, Y. R. et al. Enhancing gene delivery of adeno-associated viruses by cell-permeable peptides. Mol Ther-Meth Clin D 1, doi:Unsp 12 10.1038/Mtm.2013.12 (2014).

Liu, Y. T. et al. "Nanoparticles of lipid monolayer shell and biodegradable polymer core for controlled release of paclitaxel: Effects of surfactants on particles size, characteristics and in vitro performance." International Journal of Pharmaceutics 395, 243-250, doi:10.1016/j.ijpharm.2010.05.008 (2010).

Lungwitz, U. et al. "Polyethylenimine-based non-viral gene delivery systems." European Journal of Pharmaceutics and Biopharmaceutics 60, 247-266, doi:http://dx.doi.org/10.1016/j.ejpb.2004.11.011 (2005).

Martinez, F. O. et al. "The M1 and M2 paradigm of macrophage activation: timefor reassessment." F1000prime reports 6, 13, doi:10.12703/P6-13 (2014).

Medzhitov, R. "Origin and physiological roles of inflammation." Nature 454, 428-435, doi:10.1038/nature07201 (2008).

Miele, E. et al. "Nanoparticle-based delivery of small interfering RNA: challenges for cancer therapy." International journal of nanomedicine 7, 3637-3657, doi:10.2147/Ijn.S23696 (2012).

PCT/2018/063546 Search Report and Written Opinion dated Feb. 15, 2019.

Mimi, H. et al. "Polyethyleneimine-Based Core-Shell Nanogels: A Promising siRNA Carrier for Argininosuccinate Synthetase mRNA Knockdown in HeLa Cells." J. Control. Release 158, 123-130,doi:http://dx.doi.org/10.1016/j.conrel.2011.10.035 (2012).

Moghimi, S. M. et al. "A two-stage poly(ethylenimine)-mediated cytotoxicity: implications for gene transfer/therapy." Mol. Ther. 11, 990-995, doi:http://www.nature.com/mt/journal/v11/n6/suppinfo/mt2005120s1.html (2005).

Moncada, C. et al. "Simple Method for the Preparation of Antigen Emulsions for Immunization." J Immunol Methods 162, 133-140, doi:Doi 10.1016/0022-1759(93)90415-4(1993).

Morris, D. L. et al. "Adipose tissue macrophages: phenotypic plasticity and diversity in lean and obese states." Current opinion in clinical nutrition and metabolic care 14, 341-346, doi:10.1097/MCO.0b013e328347970b (2011).

Murray, P. J. et al. "Macrophage activation and polarization: nomenclature and experimental guidelines." Immunity 41, 14-20, doi:10.1016/j.immuni.2014.06.008 (2014).

Osborn, O. et al."The cellular and signaling networks linking the immune system and metabolism in disease." Nature medicine 18, 363-374, doi:10.1038/nm.2627 (2012).

30 min 120 min

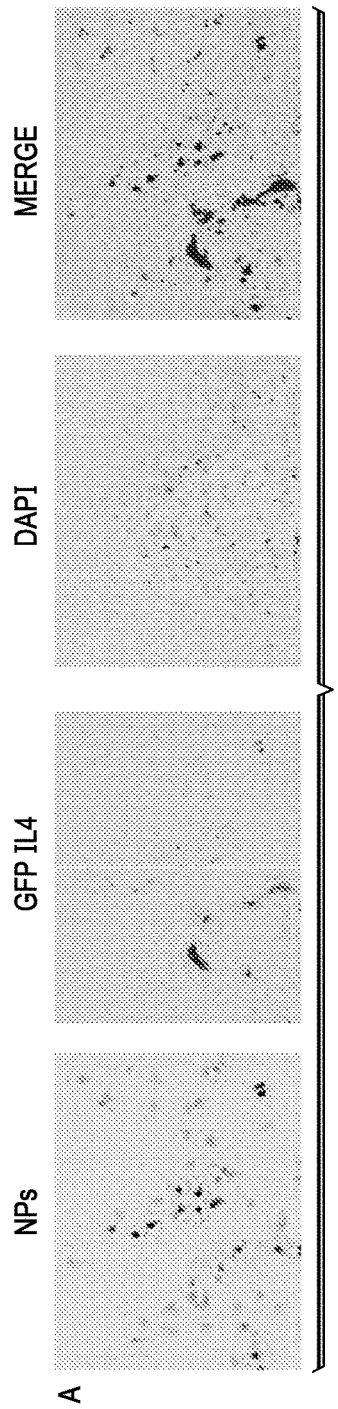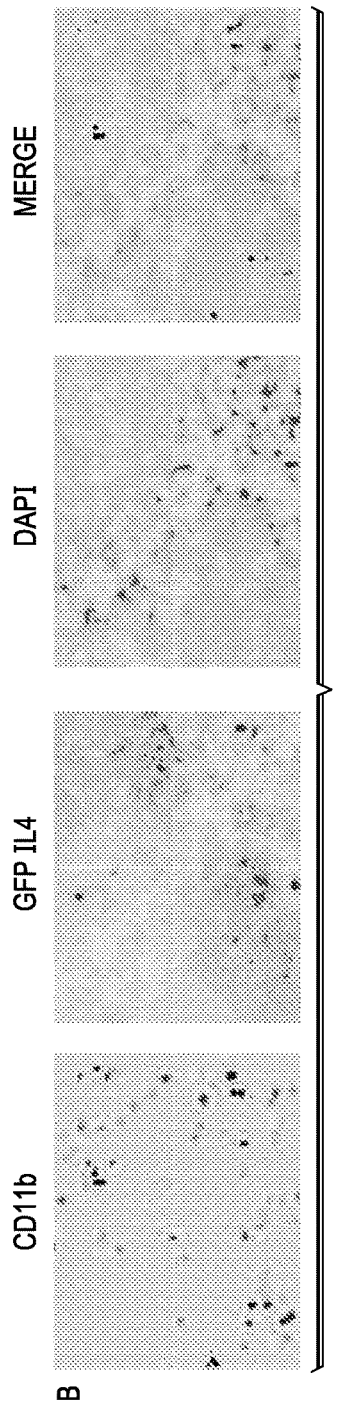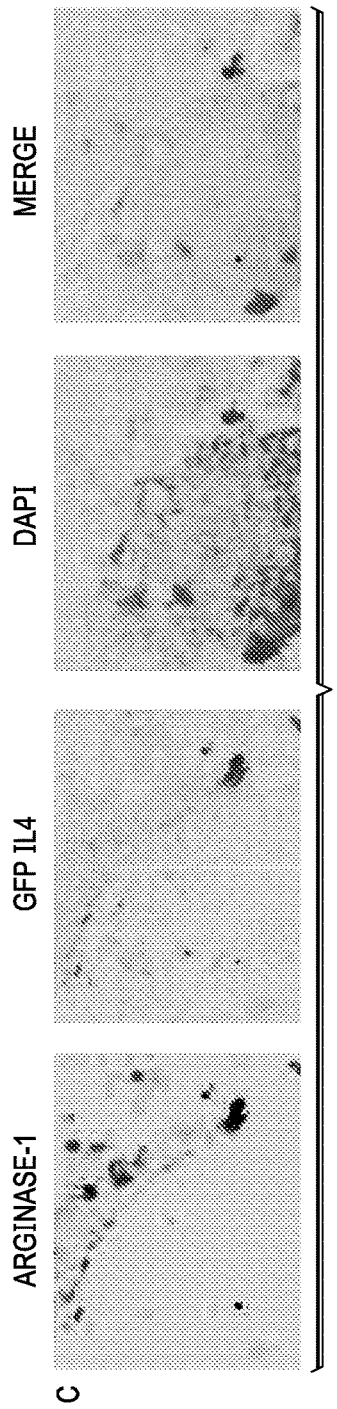

HIGH EFFICIENT DELIVERY OF PLASMID DNA INTO HUMAN AND VERTEBRATE PRIMARY CELLS IN VITRO AND IN VIVO BY NANOCOMPLEXES

CROSS-REFERENCE TO RELATED APPLICATIONS

This application is the National Stage of International Application No. PCT/US2018/063546, filed on Dec. 3, 2018, which claims priority to U.S. Patent Appl. Ser. No. 62/611,673, filed Dec. 29, 2017, the content of each of which is incorporated by reference herein.

STATEMENT OF FEDERALLY FUNDED RESEARCH

This invention was made with government support under 1R01GM114851-01A1 awarded by the National Institute of Health. The government has certain rights in the invention.

TECHNICAL FIELD OF THE INVENTION

The present invention relates in general to the field of high efficient delivery of plasmid DNA and other nucleic acids into human and vertebrate primary cells in vitro and in vitro by nanocomplexes.

BACKGROUND OF THE INVENTION

Without limiting the scope of the invention, its background is described in connection with gene delivery to monocytes.

Gene therapy has received attention as a promising method for treatment of numerous gene-associated human diseases such as cancer, neurodegenerative disease, hemophilia, hypercholesterolemia[1-6]. With this strategy, a gene was introduced into the targeted tissue or cells by modulating the expression of the genes such as up/down regulate expression and exogenous expression to cure or prevent the progression of the related disease[7,8]. However, generally, naked genetic molecules, and drug itself show low internalization efficacy in target cells because of their fast degradation in plasma and reduced intracellular uptake by target cells. Further, toxic effect arose by immune response stimulation, leading to the severe limitation of the clinical application[9]. Therefore, carriers that improve the intracellular delivery of gene by supporting the gene is a key factor to establish the delivery technologies. With the great development of materials sciences and the rapid progress of bio/nanotechnology, nanosized materials have attracted worldwide attention, expecting the enormous potential of clinical application for many human diseases[9-15].

Polyethyleneimine (PEI)-based nanodelivery systems have attracted increasing attention[19-22]. However, currently reported PEI formulations show low transfection efficacy and high toxicity[20,23-28]. An improvement in transfection efficiency with PEI largely relies on the effective condensation of pDNA by the high cationic density from high molecular PEI. But higher cationic density also brings higher cytotoxicity because of lack of backbone biodegradability. For example, 800 Da PEI has much low cytotoxicity, but almost no transfection efficacy, while 25 kDa PEI is effective in gene transfection, but also has high cytotoxicity. In order to enhance the gene delivery efficacy of PEI and to minimize its cytotoxicity, various strategies have been reported to chemically modify its polymeric backbone which bring biodegradability or reduce the positive charge of PEI. In these reports, low molecular weight PEI was cross-linked by series of diacrylate[29-31] and higher molecular weight PEI analogs with biodegradable backbones to obtained a complex with pDNA or siRNA. The hydrolysis of the ester bonds will occur under physiological conditions within the cell after transfection and convert the cross-linked high molecular weight PEI into low toxic low molecular weight PEI. By these methods, higher transfection efficacies and lower toxicities than 25 kDa PEI were achieved. Similarly, degradable PEIs with acid-labile imine linkers were synthesized from low molecular weight PEI and glutadialdehyde[27]. These PEIs rapidly degraded into nontoxic low molecular weight PEI in acidic endosome. Thus, a need remains for better compositions and methods for transfecting cells with nucleic acids.

SUMMARY OF THE INVENTION

In one embodiment, the present invention includes a transfection complex comprising: one or more polyethyleneimine800-EpoxyC8-22 (PEI800-C8-22) lipids complexed with one or more nucleic acids on or about one or more nanoparticles. In one aspect, the PEI800-C8-22 lipid is a PEI-EpoxyC16 lipid synthesized at molar ratio of 4 to 1 PEI800 to EpoxyC8-22 to 1 to 14 PEI800 to EpoxyC8-22. In another aspect, the PEI800 is a branched polyethyleneimine. In another aspect, the PEI800-C8-22 lipid is a PEI-EpoxyC16 lipid synthesized at molar ratio of 1 to 12 (PEI12C16). In another aspect, the PEI800-C8-22 lipid is a PEI-EpoxyC16 lipid synthesized at molar ratio at 1 to 8 (PEI8C16). In another aspect, the PEI800-C8-22 lipid is a PEI-EpoxyC16 lipid synthesized at molar ratio at 1 to 4 (PEI4C16). In another aspect, the PEI800-C8-22 lipid is at least one of a Polyethyleneimine800-EpoxyC16 (PEI-C16), PEI12C16, PEI8C16, or PEI4C16 lipid formed into a core-shell nanoparticle. In another aspect, the PEI800-C8-22 lipid is at least one of a Polyethyleneimine800-EpoxyC16 (PEI-C16), PEI12C16, PEI8C16, or PEI4C16 lipid formed into a liposome. In another aspect, the PEI800-C8-22 is selected from at least one of a C8, C9, C10, C11, C12, C13, C14, C15, C16, C17, C18, C19, C20, C21, or C22 lipid, mixtures, or combinations thereof. In another aspect, the nanoparticle is further defined as at least one of a biocompatible or biodegradable polymer. In another aspect, the nucleic acid is DNA or RNA, small interfering RNA (siRNA), messenger RNA (mRNA), single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (as-RNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In another aspect, the nanoparticles comprise biodegradable polymers. In another aspect, the PEI800-C8-22 lipid is an amphiphilic polyethyleneimine800 (PEI800)-EpoxyC16 (PEI-C16), PEI12C16, PEI8C16 and PEI4C16 lipids that further comprise hexadecyl tail groups. In another aspect, the PEI800-C8-22 lipid is an amphiphilic polyethyleneimine800 (PEI800))-EpoxyC16 (PEI-C16), PEI12C16, PEI8C16 and PEI4C16 lipids that further comprise polyethylene glycol groups. In another aspect, the PEI800-C8-22 lipid is an amphiphilic polyethyleneimine800 (PEI800)-EpoxyC16 (PEI-C16), PEI12C16, PEI8C16, and PEI4C16 lipids and EpoxyC16 that comprise low branched molecular weight PEI. In another aspect, the PEI800-C8-22 lipid is an amphiphilic polyethyleneimine800 (PEI800)-EpoxyC16 (PEI-C16), PEI12C16, PEI8C16, PEI4C16 lipids that comprise poly (lactic-co-glycolic acid) PLGA. In another aspect, the PEI800-C8-22 lipid is at least one of an amphiphilic polyethyleneimine800 (PEI800)-EpoxyC16 (PEI-C16), PEI12C16, PEI8C16, or PEI4C16 lipid formed in nanoparticles and liposomes comprises a nucleic acid vector, a plasmid DNA, a viral DNA, or a self-replicating DNA. In another aspect, the PEI800-C8-22 lipid is at least one of an amphiphilic polyethyleneimine800 (PEI800)-EpoxyC16 (PEI-C16), PEI12C16, PEI8C16, or PEI4C16 lipids formed on nanoparticles into liposomes and the nucleic acid vector comprises at least one of a short hairpin RNA or small hairpin RNA (shRNA/Hairpin Vector), a small non-coding RNA (miRNA), a bifunctional shRNA, or interference RNA (RNAi). In another aspect, the PEI800-C8-22 lipid is amphiphilic and is at least one of an polyethyleneimine800 (PEI800)-EpoxyC16 (PEI-C16), PEI12C16, PEI8C16, or PEI4C16 lipids complexed with one or more nucleic acid vectors have a higher efficiency of nucleic acid transfection when compared to PEI-C16-, PEI12C16-, PEI8C16-, and PEI4C16-nanoparticle complexes. In another aspect, the C8-22 lipid is at least one of a phosphatidylcholine, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC,), 1-palmitoyl-2-oleylphosphatidylcholine (POPC), 1-oleyl-2-palmitoyl-phosphatidylcholine (OPPC), dilauroyl-phosphatidylglycerol (DLPG), diarachidoylphosphatidylglycerol (DAPG), dimyristoylphosphatidylglycerol (DMPG), dipalmitoylphosphatidylglycerol (DPPG), distearoylphosphatidylglycerol (DSPG, dioleoyl-phosphatidylglycerol (DOPG), dimyristoyl phosphatidic acid (DMPA), dipalmitoyl phosphatidic acid (DPPA), distearoyl phosphatidic acid (DSPA), diarachidoylphosphatidic acid (DAPA), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified dioleylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP) and mixtures thereof. In certain aspects, the transfection complex consists essentially of one or more polyethyleneimine800-EpoxyC8-22 (PEI800-C8-22) lipids complexed with one or more nucleic acids on or about one or more nanoparticles. In certain aspects, the transfection complex consists of one or more polyethyleneimine800-EpoxyC8-22 (PEI800-C8-22) lipids complexed with one or more nucleic acids on or about one or more nanoparticles.

In another embodiment, the present invention includes a method of synthesis of amphiphilic polyethyleneimine800-EpoxyC8-22 comprising: mixing a polyethyleneimine800 (PEI800) with an EpoxyC8-22 under conditions in which a polyethyleneimine800-EpoxyC8-22 lipid is formed. In one aspect, the PEI800-C8-22 lipid is a PEI-EpoxyC16 lipid synthesized at molar ratio of 4 to 1 PEI800 to EpoxyC8-22 to 1 to 14 PEI800 to EpoxyC8-22. In another aspect, the PEI800 is a branched polyethyleneimine. In another aspect, the PEI800-C8-22 lipid is a PEI-EpoxyC16 lipid synthesized at molar ratio of 1 to 12 (PEI12C16). In another aspect, the PEI800-C8-22 lipid is a PEI-EpoxyC16 lipid synthesized at molar ratio at 1 to 8 (PEI8C16). In another aspect, the PEI800-C8-22 lipid is a PEI-EpoxyC16 lipid synthesized at molar ratio at 1 to 4 (PEI4C16). In another aspect, the PEI800-C8-22 lipid is at least one of a Polyethyleneimine800-EpoxyC16 (PEI-C16), PEI12C16, PEI8C16, or PEI4C16 lipid formed into a core-shell nanoparticle. In another aspect, the PEI800-C8-22 lipid is at least one of a Polyethyleneimine800-EpoxyC16 (PEI-C16), PEI12C16, PEI8C16, or PEI4C16 lipid formed into a liposome. In another aspect, the PEI800-C8-22 is selected from at least one of a C8, C9, C10, C11, C12, C13, C14, C15, C16, C17, C18, C19, C20, C21, or C22 lipid, mixtures, or combinations thereof. In another aspect, the PEI800-C8-22 lipid is an amphiphilic polyethyleneimine800 (PEI800)-EpoxyC16 (PEI-C16), PEI12C16, PEI8C16 and PEI4C16 lipids that further comprise hexadecyl tail groups. In another aspect, the PEI800-C8-22 lipid is an amphiphilic polyethyleneimine800 (PEI800))-EpoxyC16 (PEI-C16), PEI12C16, PEI8C16 and PEI4C16 lipids that further comprise polyethylene glycol groups. In another aspect, the PEI800-C8-22 lipid is an amphiphilic polyethyleneimine800 (PEI800)-EpoxyC16 (PEI-C16), PEI12C16, PEI8C16, and PEI4C16 lipids and EpoxyC16 that comprise low branched molecular weight PEI. In another aspect, the PEI800-C8-22 lipid is an amphiphilic polyethyleneimine800 (PEI800)-EpoxyC16 (PEI-C16), PEI12C16, PEI8C16, PEI4C16 lipids that comprise poly (lactic-co-glycolic acid) PLGA. In another aspect, the PEI800-C8-22 lipid is at least one of an amphiphilic polyethyleneimine800 (PEI800)-EpoxyC16 (PEI-C16), PEI12C16, PEI8C16, or PEI4C16 lipid and is formed with nanoparticles and liposomes into a transfection complex that further comprises a nucleic acid vector, a plasmid DNA, a viral DNA, or a self-replicating DNA. In another aspect, the PEI800-C8-22 lipid is at least one of an amphiphilic polyethyleneimine800 (PEI800)-EpoxyC16 (PEI-C16), PEI12C16, PEI8C16, or PEI4C16 lipids formed on nanoparticles into liposomes and the nucleic acid vector comprises at least one of a short hairpin RNA or small hairpin RNA (shRNA/Hairpin Vector), a small non-coding RNA (miRNA), a bifunctional shRNA, or interference RNA (RNAi). In another aspect, the PEI800-C8-22 lipid is amphiphilic and is at least one of an polyethyleneimine800 (PEI800)-EpoxyC16 (PEI-C16), PEI12C16, PEI8C16, or PEI4C16 lipids complexed with one or more nucleic acid vectors have a higher efficiency of nucleic acid transfection when compared to PEI-C16-, PEI12C16-, PEI8C16-, and PEI4C16-nanoparticle complexes. In another aspect, the C8-22 lipid is at least one of a phosphatidylcholine, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC),), 1-palmitoyl-2-oleylphosphatidylcholine (POPC), 1-oleyl-2-palmitoyl-phosphatidylcholine (OPPC), dilauroyl-phosphatidylglycerol (DLPG), diarachidoylphosphatidyl-glycerol (DAPG), dimyristoylphosphatidylglycerol (DMPG), dipalmitoylphosphatidylglycerol (DPPG), distearoylphosphatidylglycerol (DSPG, dioleoyl-phosphatidylglycerol (DOPG), dimyristoyl phosphatidic acid (DMPA), dipalmitoyl phosphatidic acid (DPPA), distearoyl phosphatidic acid (DSPA), diarachidoylphosphatidic acid (DAPA), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyletha-nolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified dioleylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP) and mixtures thereof. In certain aspects, the transfection complex consists essentially of one or more polyethyleneimine800-EpoxyC8-22 (PEI800-C8-22) lipids complexed with one or more nucleic acids on or about one or more nanoparticles. In certain aspects, the transfection complex consists of one or more polyethyleneimine800-EpoxyC8-22 (PEI800-C8-22) lipids complexed with one or more nucleic acids on or about one or more nanoparticles.

In yet another embodiment, the present invention includes a method of making a transfection complex comprising: mixing a nanoparticle with a polyethyleneimine800-EpoxyC8-22 lipid to form a nanoparticle-lipid complex; and mixing the nanoparticle-lipid complex with at least one of a DNA, an RNA, a nucleic acid vector, a shRNA, miRNA, or RNAi to form the transfection complex. In one aspect, the PEI800-C8-22 lipid is a PEI-EpoxyC16 lipid synthesized at molar ratio of 2 to 1 PEI800 to EpoxyC8-22 to 1 to 12 PEI800 to EpoxyC8-22. In another aspect, the PEI800 is a branched polyethyleneimine. In another aspect, the PEI800-C8-22 lipid is a PEI-EpoxyC16 lipid synthesized at molar ratio of 1 to 12 (PEI12C16). In another aspect, the PEI800-C8-22 lipid is a PEI-EpoxyC16 lipid synthesized at molar ratio at 1 to 8 (PEI8C16). In another aspect, the PEI800-C8-22 lipid is a PEI-EpoxyC16 lipid synthesized at molar ratio at 1 to 4 (PEI4C16). In another aspect, the polyethyleneimine800-EpoxyC8-22 lipid under conditions in which the -PEI-C16, PEI12C16, PEI8C16, or PEI4C16. In another aspect, the amphiphilic polyethyleneimine800 (PEI800)-EpoxyC16 (PEI-C16), PEI12C16, PEI8C16, and PEI4C16 lipids are formed into a liposome. In another aspect, the nanoparticles-complex comprise at least one of a biocompatible polymer or a biodegradable polymer. In another aspect, the amphiphilic polyethyleneimine800 (PEI800)-EpoxyC16 (PEI-C16), PEI12C16, PEI8C16, and PEI4C16 lipids further comprise hexadecyl tail groups. In another aspect, the amphiphilic polyethyleneimine800 (PEI800)-EpoxyC16 (PEI-C16), PEI12C16, PEI8C16, and PEI4C16 lipids further comprise polyethylene glycol groups. In another aspect, the amphiphilic polyethyleneimine800 (PEI800)-EpoxyC16 (PEI-C16), PEI12C16, PEI8C16, and PEI4C16 comprise poly (lactic-co-glycolic acid) PLGA. In another aspect, the amphiphilic polyethyleneimine800 (PEI800)-EpoxyC16 (PEI-C16), PEI12C16, PEI8C16, and PEI4C16 formed nanoparticle-complex comprises nucleic acid vector, shRNA vector, miRNA and RNAi. In another aspect, the amphiphilic polyethyleneimine800 (PEI800)-EpoxyC16 (PEI-C16), PEI12C16, PEI8C16, and PEI4C16 lipids complexed with one or more nucleic acid vectors, shRNA vectors, miRNA and RNAi have a higher efficiency of nucleic acid transfection when compared to PEI-nanoparticle complexes. In certain aspects, the transfection complex consists essentially of one or more polyethyleneimine800-EpoxyC8-22 (PEI800-C8-22) lipids complexed with one or more nucleic acids on or about one or more nanoparticles. In certain aspects, the transfection complex consists of one or more polyethyleneimine800-EpoxyC8-22 (PEI800-C8-22) lipids complexed with one or more nucleic acids on or about one or more nanoparticles.

In yet another embodiment, the present invention includes a method of transfecting primary monocytes and macrophages comprising: contacting leukocytes, myeloid cells, lymphoid cells, monocytes, macrophages and dendritic cells (DC) under conditions in which the cells are transfected in vitro or in vivo with a composition comprising one or more nanoparticles and at least one of a polyethyleneimine800-EpoxyC8-22, an amphiphilic polyethyleneimine800 (PEI800)-EpoxyC16 (PEI-C16), PEI12C16, PEI8C16, or PEI4C16 lipids, complexed with one or more nucleic acid vectors, shRNA vectors, miRNAs, DNA, plasmid DNA, or RNA, on or about the nanoparticles-complexes.

In yet another embodiment, the present invention includes a method of making an amphiphilic polyethyleneimine800 (PEI800)-EpoxyC16 (PEI-C16), PEI12C16, PEI8C16, and PEI4C16 lipid-nanoparticle complex comprising: mixing a low molecular weight polyethyleneimine800-EpoxyC8-22, polyethyleneimine800 (PEI800)-EpoxyC16, PEI12C16, PEI8C16, and PEI4C16 with one or more lipids under conditions in which the PEI reacts with the lipids to form amphiphilic PEI lipids; and mixing the amphiphilic PEI lipids with nanoparticles under conditions in which the PEI lipids form liposomes and attach to the nanoparticles to form amphiphilic polyethyleneimine800-EpoxyC8-22, polyethyleneimine800 (PEI800)-EpoxyC16 (PEI-C16), PEI12C16, PEI8C16, and PEI4C16 lipid-nanoparticle complexes.

DESCRIPTION OF THE DRAWINGS

For a more complete understanding of the features and advantages of the present invention, reference is now made to the detailed description of the invention along with the accompanying figures and in which:

FIG. 2A, the morphologies of nanoparticles (NPs) with and without DNA combining via SEM and AFM. FIG. 2B, physical properties such as size, zeta potential and PDI of the obtained NPs with and without DNA. FIG. 2C, Agarose gel electrophoresis assay of complexation NPs with DNA at various molar ratios of NPs to DNA. Lane 1: 0.2 μg PLB plasmid; Lane 2: NPs:DNA=1:1; Lane 3: NPs:DNA=1:10; Lane 4: NPs:DNA=1:20; Lane 5: NPs:DNA=1:50.

FIG. 5A shows Microscopy images of human cells treated with DNA-NPs complexes (1.5 ng/mL of complexes, NP:DNA=1:20) post 3 and 5 days transfection. The nuclei were stained with DAPI (blue), NPs were labelled with rodamine (red), and the green fluorescence revealed transfection. FIG. 5B shows confocal images of human cells treated with DNA-NPs complexes (1.5 ng/mL of complexes, NP:DNA=1:20) post 5 days transfection. The nuclei were stained with DAPI (blue), DNA was labeled with BOBO-1 (red), and the green fluorescence revealed transfection. The yellow spot in the merged image indicated the combination of transfection and DNA. The upper right panel indicated microscopy intensities of nuclei, DNA and transfection verse the location. The lower panel presented the confocal images and microscopy intensities of the nuclei, DNA and transfection verse the location.

FIG. 8D and FIG. 8H were high magnification SEM images from FIG. 8B and FIG. 8F. The magnification of confocal image is 100×.

FIG. 9A to 9C show histology of transplanted cells. FIG. 9A shows microscopy images of mice treated with DNA-NPs post 7 days transfection. FIG. 9B shows tissue distribution of IL-4 (green) and CD 11b (red) in spleen. FIG. 9C shows tissue distribution of IL-4 (green) and M2 macrophages (red). Note that arginase-1 is a marker for M2 macrophages.

DESCRIPTION OF THE INVENTION

Figure 1A:
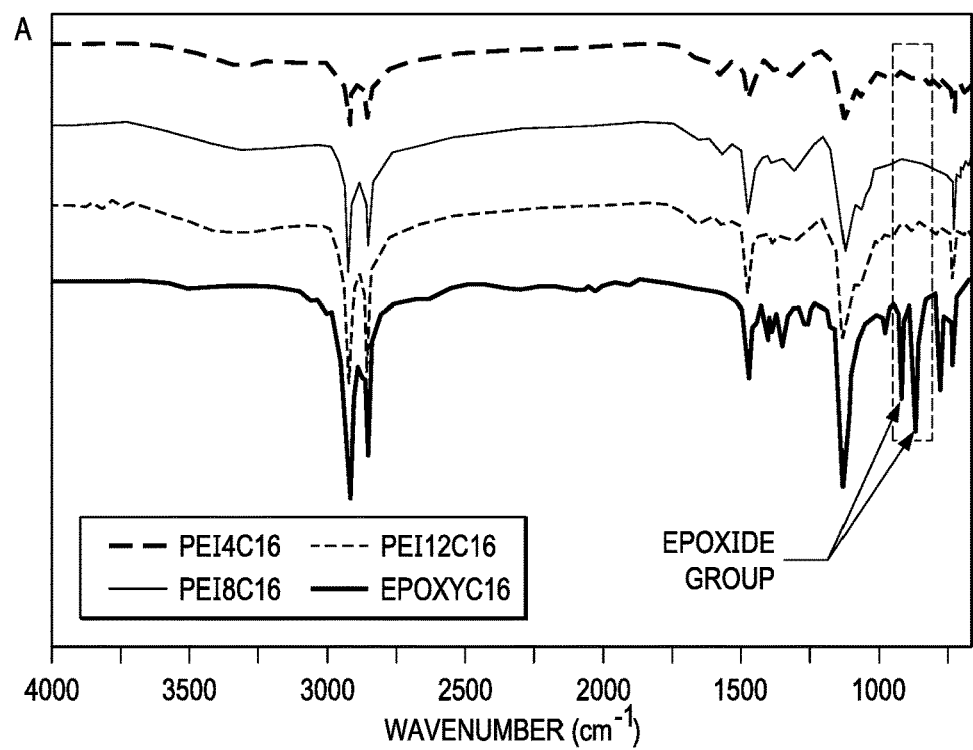
FIG. 1A shows FT-IR spectra of EpoxyC16, PEI4C16, PEI8C16 and PEI12C16.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Macrophages play many key roles in various human diseases, as such, the study of macrophage-targeted plasmid DNA delivery has received growing attention for vaccine, anti-cancer, anti-inflammation and neuroprotection gene therapies. However, delivery of DNA to integrate into primary cell genome, in particular macrophage, is especially difficulty. Therefore, high efficient delivery is a key for DNA transection in primary cells and in vivo.

To improve the delivery of plasmids to specifically target macrophages, polyethyleneimine (PEI) lipids, with low molecular weight PEI as headgroup and hexadecyl chain as tail group, were prepared through highly efficient ring-opening reaction of glycidyl hexadecyl ether (EpoxyC16) by amine from PEI. These PEI lipids were used as surfactant to coat poly(D,L-lactide-co-glycolide) (PLGA) core for developing DNA loaded core-shell nanocomplex. The synthesized nanocomplexes were high encapsulation and positive charge with size arrange from 58-250 nm according to desirable design. Thus, the present invention includes a simple, tunable method for the preparation of DNA delivery platforms by complexes, leading to high effective transfection in human blood monocytes derived macrophages (MDM), mouse bone marrow derived macrophages (BMM) and in mouse. In addition, the present invention includes expression of targeting DNA regulated the macrophage plasticity and adjusted the functional secretions, expecting the application in gene therapy for clinical purpose.

The present inventors selected the low molecular weights of polyethyleneimine (PEI), which exhibit a high positive charge density in protonated aqueous solution, and considered to be promising candidate as nonviral vectors for delivery of DNA and oligonucleotides because the relatively high efficiency of PEI to have a high amine density and buffering capacity. As a result of electrostatic interaction between the ammonium groups of the polycation of PEI and phosphate groups of the nucleic acids (such, as DNA and RNA), the PEI and nucleic acid forms complexes. Especially, branched low molecular weight of PEI was reported to be associated with successful gene delivery with various cells, initiated in vivo transfection and revealed the low toxicity.

In this study, the inventors used a highly efficient ring-opening reaction of epoxide by the amine group for the modification of low molecular weight PEI with long alkyl chain lipids and obtained amphiphilic PEI lipids with different amount of hexadecyl tail groups (PEI lipids).

These PEI lipids were further used for the formulation of cationic liposomes by simple sonication method and also as surfactant in the PLGA nanoparticle via solvent extraction/evaporation method.[38,39] The properties of these two types of gene delivery platforms were systematically studied. Through the physical self-assembly of low molecular weight PEI on the surface of nanoparticles, higher transfection efficacy and lowered toxicity as compared to high molecular weight PEI 25 kDa in both facile gene delivery platforms were realized. Although PEI-based nanoparticle as gene delivery system has been reported before,[40] the PEI lipids of the present invention used highly efficient chemistry to form component of liposome and/or as a surfactant or coating for PLGA nanoparticles as effective gene delivery platform has never been reported.

The present invention is a facile gene delivery platform derived from low molecular weight PEI by highly efficient chemistry. Another component that can be added is a high performance nanoparticles that is, e.g., biodegradable and/or biocompatible polymer or poly (lactic-co-glycolic acid) (PLGA). PLGA have negative charge that results in low transport through the extracellular membrane. However, the modified PLGA with a cationic agent such as PEI have the enriched steric PEI chains on the surface[41]. In turn, PEI modified PLGA shown the enhancement of gene transfer due to the retain DNA in tissues and improvement of the cellular transport and intracellular uptake due to the enhanced permeability. Therefore, PEI modified PLGA nanoparticles have attracted increasing attention for in vivo pharmacokinetic and biomedical area.

Macrophages, a type of the mononuclear phagocyte, are present in almost all tissues of human body and play critically important role to tissue injury response and reservoir for pathogens in the innate immune system[42-44]. Since macrophages act as a host defense, they modified molecules and exogenous agents, resulting in phagocytosis or endocytosis, intracellular signaling and complexes changes in gene activation and repression[45,46]. Therefore, macrophages strongly involved in immunity and inflammatory responses, relating with maintaining homeostasis of the body and modulating inflammatory response. Macrophage based gene therapy is a promising for preventing or curing the divers human diseases such as cancer, range of blood-vascular disorder, diabetes and divers immune disorders. Despite these positive prospects, the transfection of macrophages remains a long-standing challenge because macrophages are hard to transfect, e.g., as primary cells, due to the significant intracellular ROS production, which is detrimental to plasmid integrity[47,48]. Therefore, in order to break through this, chemically modified nanoparticles to occur the cellular internalization, endosome interruption and transfection has been attracted, positively charged nanoparticles in particular.

The present invention includes a simple, one-step method for fabrication of positive charged nanoparticles with low molecular weights of PEI by using a vortexing treatment. In addition, using the obtained nanoparticles, the inventors systematically investigated the approaches to apply for gene therapy on macrophages based on the relation between the physiochemical properties of nanoparticles and efficacy of the gene delivery.

Synthesis of the nanoparticles. For synthesis of the nanoparticles, low molecular branched polyethylenimine (PEI800, Mn 600), glycidyl hexadecyl ether (MW 298) and dichloromethane (DCM) were obtained from Sigma. Hydrogenated soybean phosphatidylcholine (HSPC, MW 762) was purchased from Avanti Polar Lipids. 1,2-Dimyristoyl-sn-glycerol, methoxypolyethylene Glycol (DMG-PEG, 2000) was purchased from NOF America. Poly(D,L-lactide-co-glycolide) (50/50) with terminal carboxylate groups (PLGA; inherent viscosity, 0.55-0.75 dl/g in hexafluoroisopropanol; MW 44 kDa) was obtained from Absorbable Polymers International. For the study of the dynamic action between the NPs-DNA complexes and cells, YOYO-1, BOBO-1 and LysoTracker Red were purchased from Thermo Fisher Scientific. For the study of the cell viability, 4-[3-(4-iodophenyl)-2-(4-nitrophenyl)-2H-5-tetrazolio]-1,3-benzene disylfonate (WST-1) was purchased from BioVision. For histochemical study, IL-4 and CD11b were obtained from abcam (Cambridge, Mass., USA) and arginase-1 was obtained from thermo Fisher Scientific (Waltham, Mass. USA). For the secondary antibodies, Alexa fluor 488, and 594 were obtained from thermo Fisher Scientific (Waltham, Mass. USA). DAPI (SlowFade® Gold Antifade Mountant) for staining of the nuclei was obtained from termoFisher scientific (Waltham, Mass. USA).

Synthesis of PEI lipid. The fixed molar ratio of 8/1 of Glycidyl hexadecyl ether (MW=298) and branched PEI800 were mixed in a glass vial. The vial was sealed and stirred at 40° C. for 24 h. After 24 h, the vial was cooling down at room temperature by obtaining the white solids, resulting in the PEI lipids.

Synthesis of PLGA/PEI nanoparticles. PLGA/PEI nanoparticles (NPs) were prepared by a modified solvent extraction/evaporation method. 25 mg of PEI lipodoid, 15 mg of PLGA and 2 mg of DMG-PEG were dissolved in 0.5 mL of DCM. The clearly dissolved the solution was mixed with 2.5 mL of DD water. In order to obtain the fine emulsion, the vortexing process applied with different time variation at room temperature. After vortexing process, the emulsion was overnight stirring to obtain the suspension. The suspension was washed out with DI and adjusted 2.5 mL of DI to obtain a stock NPs suspension and stored at 4° C.

Preparation of NPs/DNA Complex. The NPs/DNA complexes were prepared by the obtained NPs and plasmid DNA with various ratios. Note that the NPs volume was dependent on the (±) charge ratio. NPs suspension (0.1 μg/μL) was mixed with DNA solution in PBS and further incubated for 30 min at RT.

Characterization of the obtained NPs. Changes in the morphologies of the obtained nanoparticles were observed by using a scanning electron microscope (SEM: JEOL JSM-6010LA, Tokyo, Japan). In order to avoid the broken down the NPs, the inventors dropped onto the cover glass 50 ml of NPs and added a drop of 2% of uranyl acetate (Cat. No. 22400, Electron Microscopy Sciences Hattfield, Pa.) for 15 min. Then the slide was washed out with DI, and the sample kept in the vacuum desiccator to dry out for 24 h.

The dried samples were coated with gold/Palladium using Gold/Palladium Target 57 mm diameter×0.1 mm thick (Gold/Palladium Target: Electron Microscopy Sciences Cat. No. 91017PD) with research grade argon gas. (EMS Quorum EMS 150R ES sputter coater Laughton, East Sussex, United Kingdom) to observe SEM, which were operated at 15 kV with top view.

To measure the average size and distribution of the NPs, a Malvern Zetasizer Nano ZS Dynamic Light Scattering (DLS) instrument was used. The shape, surface morphology and surface charge and distribution of the NPs were investigated by atomic force microscopy (AFM, Park XE-100 AFM. Park system, Santa Clara, Calif., USA).

Cell culture and treatment. Peripheral Blood CD14+ Monocytes (Lonza Walkersville Inc, USA) were cultivated in Dulbecco's modified Eagle Medium (Gibco) supplemented with 10% fetal bovine serum (gibco), 1% penicillin-streptomycin (Gibco), 10% heat-inactivated pooled human serum (gibco), 2 mM L-Glutamine (Gibco), 1000 U/ml highly purified recombinant human macrophage colony stimulating factor (R&D Systems) at 37° C., 5% $CO_2$. Monocytes were seeded into standard tissue culture-treated plates in macrophage media at a density of 1 million cells per ml. After 3 and 5 days differentiation in growth medium (above), half of medium exchanged with fresh media. At the 7th day, the obtained monocytes were used in these studies.

In order to find some of the best condition of transfection, the inventors set up 2 different kinds of conditions: (1) various concentrations of the NPs-DNA complexes (6, 3, 1.5, and 1.0 ng/mL), (2) various ratio of the volume of NPs-DNA complexes and medium (1:1, 1:4, 1:10, 1:20 and 1:50). In order to make NPs-DNA complexes, NPs and DNA mixtures with various concentrations incubated for 30 min at RT. Note that the used DNA is interleukin 4 (IL-4), which included a GFP plasmid. For all transfection studies the selected condition of NPs-DNA complexes were added into each well as shown. After 4 h, the media replaced with fresh medium (above) and further cultured. GFP expression was used as the evidence of transfection was observed by Nikon Ti fluorescence microscopy (Nikon Instruments Inc., Melville, N.Y.). The transfected percentages were analyzed with selected 3 pictures by Image-Pro Analyzer 7.0 software. For quantification of proportion, BD FACS Canto II flow cytometry was used to determine the GFP positive cell percentage and GFP fluorescence intensity, and Flowjo software was used to analysis. For sampling for flow, the cells were harvested with trypsin (Gibco) and cell scraper (corning).

In order to evaluate the cytotoxicity, WST-1 Cell Proliferation Assay Kit (Biovision) was used. Culture cells in a 96 well microtiter plate in a final volume of 100 ul/well culture medium, and then incubated for 24 h. After 24 h incubating, 10 ul of WST-1/ECS solution was prepared and manually added in each well, then further incubated for 4 h. Before measuring the absorbance, the plate thoroughly was shaking for 1 min on a shaker. Finally, the absorbance of the plate was measured with a microplate reader at 450 nm.

In order to verify the cytokine levels in supernatants, Human IL-4 enzyme linked immunosorbent assays (ELISA) was performed. The supernatants of post 1, 3 and 5 day transfection were used as samples, and the samples were carried out with a commercial Human IL-4 ELISA Ready-SET-Go kit (ebioscience), and quantified according to the manufacturer's instructions.

Test of cells stability. In order to track the stability of cells that were treated with the selected conditions, cells were observed for 30 days using microscopy. The cell stability after transfection was evaluated by quantification of intensity of GFP expression with Nikon Ti fluorescence microscopy analysis program.

In vitro Cellular uptake of DNA-NPs complexes. The performance of cellular uptake behavior of DNA-NPs complexes was observed by GFP expression, NPs and nuclei. Briefly, the process of cell culture of Peripheral Blood CD14+ Monocytes was same as described in section of Cell culture and treatment. After 7 days, the obtained monocytes seeded into 8 wells chamber slide (Lab-Tek® ll Chamber Slide™, nunc) for 24 h at 37° C., 5% $CO_2$. And then, the complexes made of rodamine labeled NPs and DNA with the ratio of NPs:DNA at 1:20 were loaded as 1.5 ng/mL in each well. After 4 h, the cells were washed out and immediately replaced with the fresh media. To stabilize transfection, the cells were further incubated for 7 days at 37° C., 5% $CO_2$. After 7 days, the cells were fixed with 4% papraformaldehyde for 5 min. The nuclei were stained using DAPI (SlowFade® Gold Antifade Mountant, ThermoFisher scientific) for 10 min at RT. The relation of the cellular association and intracellular location of complexes were observed by confocal laser microscope (Nikon Ti fluorescence microscopy, Nikon Instruments Inc., Melville, N.Y.). For the study of the site of the internalization in the cells, DNA was labeled with BOBO-1 (Fisher).

Intracellular trafficking of NPs. Cells were cultured as described above on the 8 wells chamber slide (Lab-Tek® 11 Chamber Slide™, nunc) for 24 h at 37° C., 5% $CO_2$. Note that the condition of treatment was as follow; the ratio of NPs:DNA=1:20, and the concentration of complexes=1.5 ng/mL. DNA was labeled with YOYO-1 as the manufacturer's protocol, was then added into NPs to formulate the complexes. The complexes were loaded to the cells and incubated for the time indicated. To track the endocytic pathway, the cells were labeled with Lysotracker Red (Life Technologies Ltd) according to the manufacture's protocol. Then, immediately, the cells were fixed with 4% paraformaldehyde. DAPI was used to stain the nuclei. The intracellular behavior was visualized using a confocal laser microscope (Nikon Ti Eclipse microscope with A1 confocal, Nikon Instruments Inc., Melville, N.Y.). Lasers at 488 and 561 nm were used to excite the DNA and Lysotracker Red, respectively.

To determine the morphology of the cells with the complex, scanning electron microscopy (SEM) was carried out with the fractured cells. The fractured cells were prepared by adhesion of cover glass. In brief, another cover glass was attached very tightly to the sample cover slips, then pulled out the added cover glass mechanically, then dried out in the vacuum desiccator for 24 h at RT. The dried samples were coated with gold/Palladium using Gold/Palladium Target 57 mm diameter×0.1 mm thick (Gold/Palladium Target: Electron Microscopy Sciences Cat. No. 91017PD) with research grade argon gas. (EMS Quorum EMS 150R ES sputter coater Laughton, East Sussex, United Kingdom) to observe SEM, which were operated at 15 kV with top view.

In vivo tissue distribution and Histological Analysis. All mouse studies were approved by the Texas Tech University Health Sciences Center, Institutional Animal Care and Use Committee (IACUC). Nude mice were purchased from the Jackson Laboratories and used at 6-8 weeks of age. The rodamine labeled DNA-NPs complexes was injected into the tail vein of nude mice at a dose of 100 mL. At day 7 post injection, the mice were humanely euthanized and the principal organs (spleen) were collected and embedded in a gel like medium consisting of polyethylene glycol and polyvinyl alcohol and frozen rapidly to about −80° C. For each mouse, 20 serial (5 mm thick) sections were prepared for staining. Slides of sectioned organs were mounted with 40,6-diamidino-2-phenylindole (DAPI) and images were acquired with a microscope (Nikon Instruments Inc., Melville, N.Y.).

For histochemical studies, the major organs such as spleen was harvested, and fixed in the mixture of 50% of methanol and 50% of acetone. Following that, they were embedded in paraffin, and approximately 5 mm thick sections were cut. To detect the distribution of tissue, IL-4, CD 11 b, and M2 macrophages were detected by immunofluorescence. Antibody to IL-4 (1: 200; abcam, Cambridge, Mass., USA), CD 1b (1:200; abcam, Cambridge, Ma, USA) and arginase-1 (1:200; Thermo Fisher Scientific, Waltham, Mass. USA) were used with corresponding Alexa fluor 488, and 594 (Thermo Fisher Scientific, Waltham, Mass. USA) as secondary antibodies. The nuclei were stained with DAPI. Immunofluorescence images were observed by a microscope (Nikon Instruments Inc., Melville, N.Y.).

Synthesis of PEI lipid. Lipids with PEI as headgroup[53] and hexadecyl chain as tail group were synthesized by reaction of EpoxyC16 with amine group from PEI.[54-56] This ring-opening reaction of epoxide by amine group was carried out under mild condition without any solvent. And it is highly efficient and specific, yielding product with negligible impurities. Compared with similar modification process, no further purification is needed.[40] One mole of branched PEI800 approximately has 18 mole amine groups in which 4.5 mole (25%) are tertiary amines, 9 mole (50%) are secondary amines and 4.5 mole (25%) are primary amines according to the information provided by supplier. Both secondary amine and primary amine can react with epoxide group. One secondary amine group can react with one equivalent amount of epoxide group and one primary amine group is capable of engaged in two ring opening reactions. Next, one mole of PEI800 can theoretically react with 18 mole of EpoxyC16. In this study, the inventors fixed the molar ratio between EpoxyC16 and PEI800 as 12 to 1, 8 to 1 and 4 to 1. Under these three feed ratio, the reactions went smoothly without any solvent at 40° C. After 24 h reaction, the inventors labeled the products as PEI4C16, PEI8C16, and PEI12C16. The products were characterized by $^1$H NMR, FT-IR and SEC. From the $^1$H-NMR spectra of products without any purification steps, the inventors recorded sharp signals from the protons of epoxide group disappeared and signals from the C16 chain such as δ=1.6 ppm had shift to the high field. By comparing the FT-IR spectra (FIG. 1A) of the three products with the starting material EpoxyC16, the inventors can see that the characteristic peaks of epoxide group at 850 cm$^{-1}$ and 910 cm$^{-1}$ fully disappeared in the spectra of products. FT-IR spectra indicated that Epoxy C16 was fully reacted with PEI800 and no EpoxyC16 left in the unpurified products.

Figure 1B:
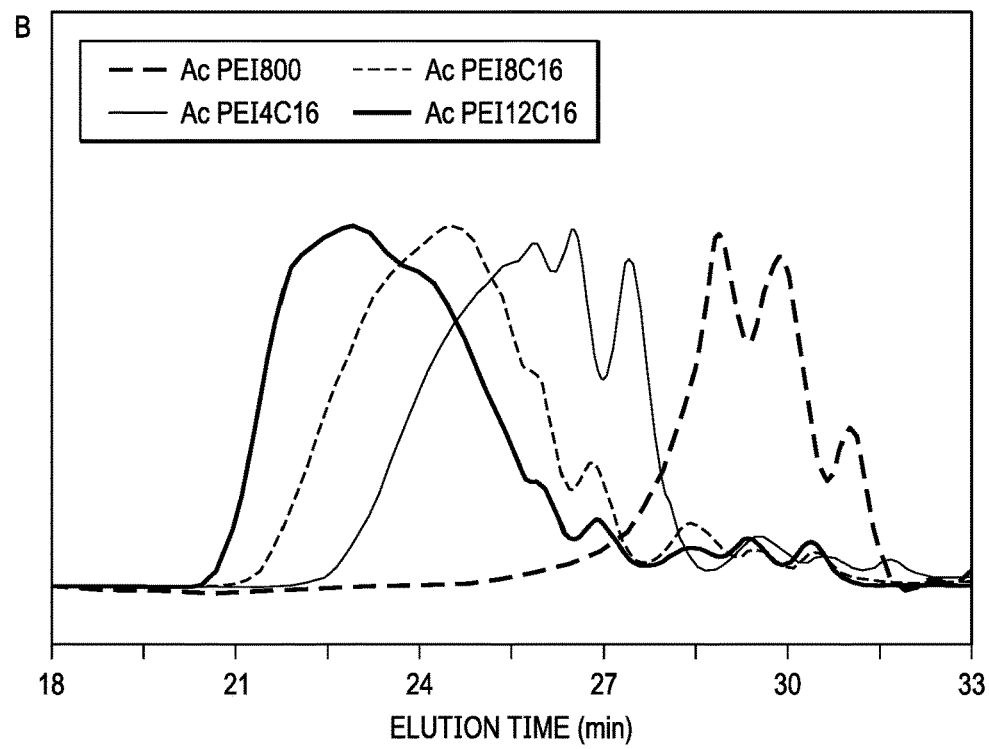
FIG. 1B shows THF SEC elution curves of Ac PEI800, Ac PEI4C16, Ac PEI4C16 and Ac PEI4C16.

In order to characterize the molecular weight and molecular weight distribution of the obtained products by THF SEC, their acetylation derivatives were prepared. From SEC elution curves (FIG. 1B) of acetylation derivatives of PEI800, PEI4C16, PEI8C16 and PEI12C16 (labeled as Ac PEI800, Ac PEI4C16, Ac PEI4C16 and Ac PEI4C16, respectively), the inventors can see that these three obtained PEI lipid had different molecular weight and molecular weight distribution from the original PEI800, indicating that there was no unreacted PEI800 left in the products and PEI800 was fully modified by reaction with EpoxyC16.

The skilled artisan will recognize that the epoxy may be an EpoxyC8, Epoxy C9, Epoxy C10, Epoxy C11, Epoxy C12, Epoxy C13, Epoxy C14, Epoxy C15, Epoxy C16, Epoxy C17, Epoxy C18, Epoxy C19, Epoxy C20, Epoxy C21, Epoxy C22, the carbon chains can be saturated or unsaturated, branched or unbranched. The C8 to C22 portion of the lipid may be phosphatidylcholine, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC,), 1-palmitoyl-2-oleylphosphatidylcholine (POPC), 1-oleyl-2-palmitoyl-phosphatidylcholine (OPPC), dilauroyl-phosphatidylglycerol (DLPG), diarachidoylphosphatidyl-glycerol (DAPG), dimyristoylphosphatidylglycerol (DMPG), dipalmitoylphosphatidylglycerol (DPPG), distearoylphosphatidylglycerol (DSPG, dioleoyl-phosphatidylglycerol (DOPG), dimyristoyl phosphatidic acid (DMPA), dipalmitoyl phosphatidic acid (DPPA), distearoyl phosphatidic acid (DSPA), diarachidoylphosphatidic acid (DAPA), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified diol-eylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP) and mixtures thereof.

Thus, three PEI headgroup lipids with different amount of hexadecyl tail groups were obtained with convenience and high purity by ring-opening reaction of epoxide by PEI800.

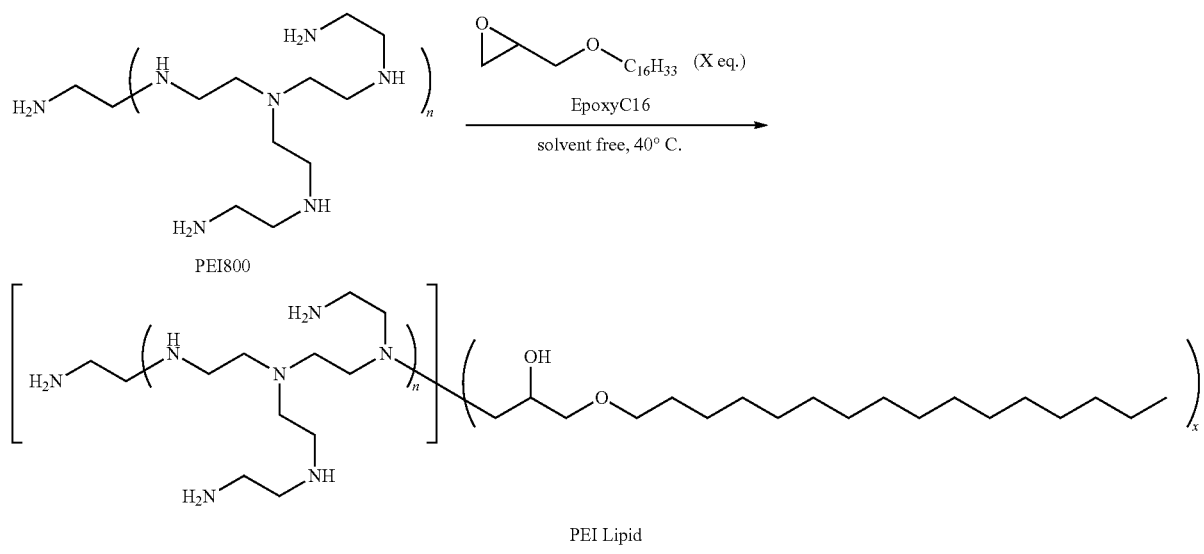

Scheme 1 shows the synthesis of PEI lipid by highly efficient reaction of EpoxyC16 with PEI800.

Preparation and characterization of PEI liposome and PEI-PLGA nanoparticles. Liposomes were made from PEI lipid, HSPC and a polyethylene glycol modified lipid, DMG-PEG. DMG-PEG (1,2-Dimyristoyl-sn-glycerol, methoxypolyethylene Glycol), which will provide the polyethyleneglycol (PEG) corona for the formed liposome, was used to increase the stability of PEI liposome in medium. Without extrusion or microfluid method, liposomes within nano range size were simply prepared by hydration and sonication. After a series of tentative transfection experiments, the inventors found that higher mass percentage of PEI headgroup to the liposome composition was relevant to the final transfection efficacy. The transfection efficacy of PEI liposomes was very low (less than 0.5% GFP positive cell) when the mass percentage of PEI headgroup to the liposome composition was less than 8.3%. Thus, the inventors tried to elevate the ratio of PEI lipid in the liposome composition. The mass percentage of PEI headgroup was successfully elevated to 18.6% or higher in the liposome made from PEI4C16. The diameter and zeta potential of resultant liposome were 75.24 nm and +32.0 mV. The mass ratio of PEI headgroup can be elevated to 15.7% in the liposome made from PEI8C16. The diameter and zeta potential of resultant liposome were 115.1 nm and +37.93. One sample of PEI12C16 liposome was made at the mass ratio of PEI headgroup as 8.8%. The diameter and zeta potential of resultant liposome were 148.5 nm and +43.13 mV. However, PEI12C16 was not capable of forming particles smaller than 400 nm when the mass percentage of PEI headgroup was higher than 10%. All of these PEI liposomes had positive zeta potential value, indicating their cationic nature.

The obtained PEI lipid, with its amphiphilic nature, can be a very good surfactant. And, the inventors successfully used PEI8C16 as surfactant in the preparation of PLGA nanoparticle by solvent extraction/evaporation method.[38,39] It can be envisaged that the obtained PLGA nanoparticle (PEI-PLGA NP) has a PLGA core with C16 chains inserted in and a cationic PEI shell (Scheme 1). In this study, the obtained PEI-PLGA NP has the diameter and zeta potential of 146.36 nm and +41.1 mV respectively. The positive zeta potential value was in agreement with the structure of the obtained PEI-PLGA NP with a cationic PEI shell. Taking advantage of this unique structure, co-delivery[57,58] of hydrophobic small molecules encapsulated in the PLGA core and gene molecules complexed with the PEI shell might be easily realized.[19,59]

TABLE 1

Preparation and characterization of PEI liposome and PEI-PLGA nanoparticles

| | Formulation (PEI lipid/HSPC/DMG-PEG/PLGA) (mg) | PEI mass percentage (%) | Size (nm) | PDI | Zeta potential (mV) |
|---|---|---|---|---|---|
| PEI12C16 LIPO | 27.5/27.5/2/0 | 8.8 | 148.5 ± 1.36 | 0.13 | +43.13 ± 0.80 |
| PEI8C16 LIPO | 20/10/2/0 | 15.7 | 115.10 ± 1.56 | 0.25 | +37.93 ± 0.76 |
| PEI4C16 LIPO | 12.5/12.5/2/0 | 18.6 | 75.24 ± 1.92 | 0.20 | +32.0 ± 1.63 |
| PEI-PLGA NP | 25/0/2/15 | 15.0 | 146.36 ± 1.89 | 0.18 | +41.1 ± 1.05 |

Figure 2A:
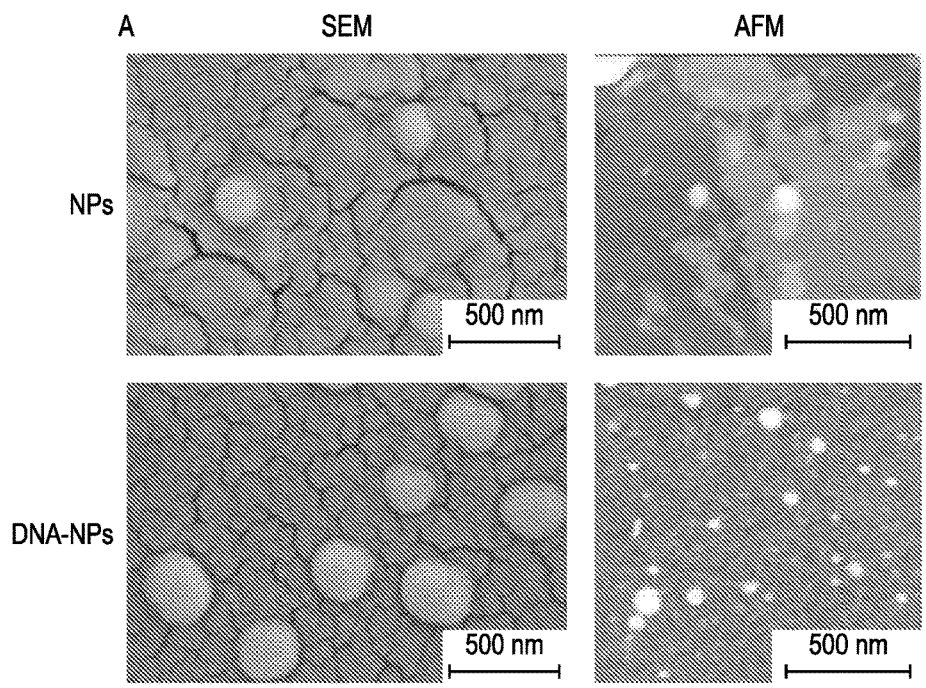
FIGS. 2A to 2C show the characterization of the obtained nanoparticles.
Figure 2B:
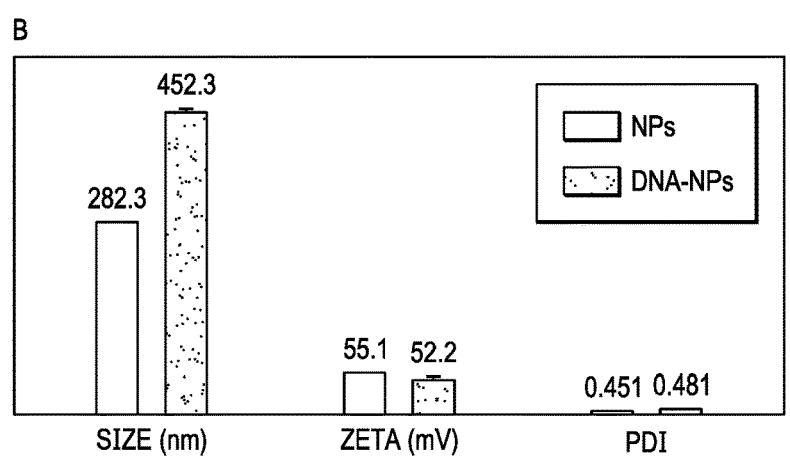
Figure 2C:
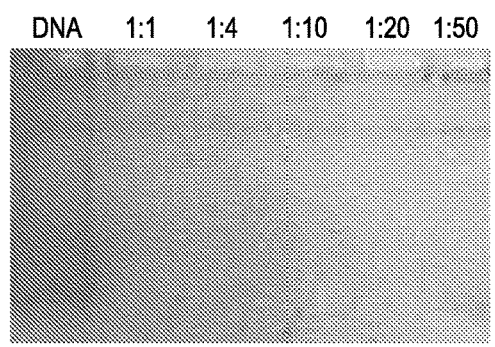

Plasmid DNA loaded PEI-PLGA Nanoparticles (DNA-NPs). NPs with the obtained PEI lipid and PLGA were successfully made. By way of explanation, and in no way a limitation of the present invention, the PEI lipid may act as a surfactant in the synthesis of NPs by solvent extraction/evaporation method[38,39]. The obtained NPs were made of a PLGA core with C16 chains, which inserted in a cationic PEI shell. In order to down size the NPs, vortexing significantly influenced the NPs fabrication, achieving the size of 100~300 nm. In case of using the different kinds of phases of materials to synthesize the emulsions, there are some drawbacks such as control the temperatures, complicate supplies and loss of products and so on[60,61]. However, the vortex method of preparing emulsions is a simple, short process and cheap, as well as no cooling condition because of no temperatures dependence[62]. Interestingly, with up to 90 min of vortexing, the size reduced in nanoscale and the values of the zeta potential increased due to the enlarged surface area. This indicated that various sizes and zeta potentials can be synthesized by fine-tuning the vortexing time. In order to synthesize the DNA-NPs complexes, electrostatic interaction between the positive charged NPs and negative charged DNA has to occur, therefore the physicochemical properties of NPs is an important factor. Note that the positive value of zeta potential value is consistent with the structures of the NPs due to a cationic PEI shell. Moreover, after making the DNA-NPs complexes, zeta potential of the complexes revealed still high positive value as 52.2 mV, respectively. It is an important property for cellular uptake because the cell membrane is negatively charged[63,64]. In addition, the proper size of the NPs and DNA-NPs complexes are one of the key factor to elaborating the efficiency of the cell uptake. Since the size of nucleus is around 1 mm to 10 mm[65], if the inventors expect the penetration of NPs to the nucleus, the minimum required size of DNA-NPS complexes is <1 mm. On the basis of this, 10 min vortexing treated NPs which showed high-positive surface charge in nanoscale were selected as the best condition in this study. SEM and AFM were used to characterize the morphology of NPs and DNA-NPs (FIG. 2A). The size of the synthesized NPs was <300 nm and the DNA-NPs were around 450 nm due to the supporting of the DNA. In addition, the dispersion of both of materials was under 1.0, which means that these suspensions were in a stable state (FIG. 2B). In order to determine the optimal conditions for the complex formation, the degree of binding between the cationic NPs and DNA at varying molar ratios of DNA-NPs was investigated using a gel retardation assay. FIG. 2C showed the visualized agarose gel electrophoresis of the formation of DNA-NPs complexes. If the complex formation can completely occur at the ratio, the DNA migration disappears[66]. The result indicated that the formulation of cationic NPs were able to condense with DNA above the ratio of 1:1. Based on the results of synthesis parts, NPs and DNA-NPs complexes were successfully obtained with low molecular weight PEI by vortexing modification.

Figure 3:
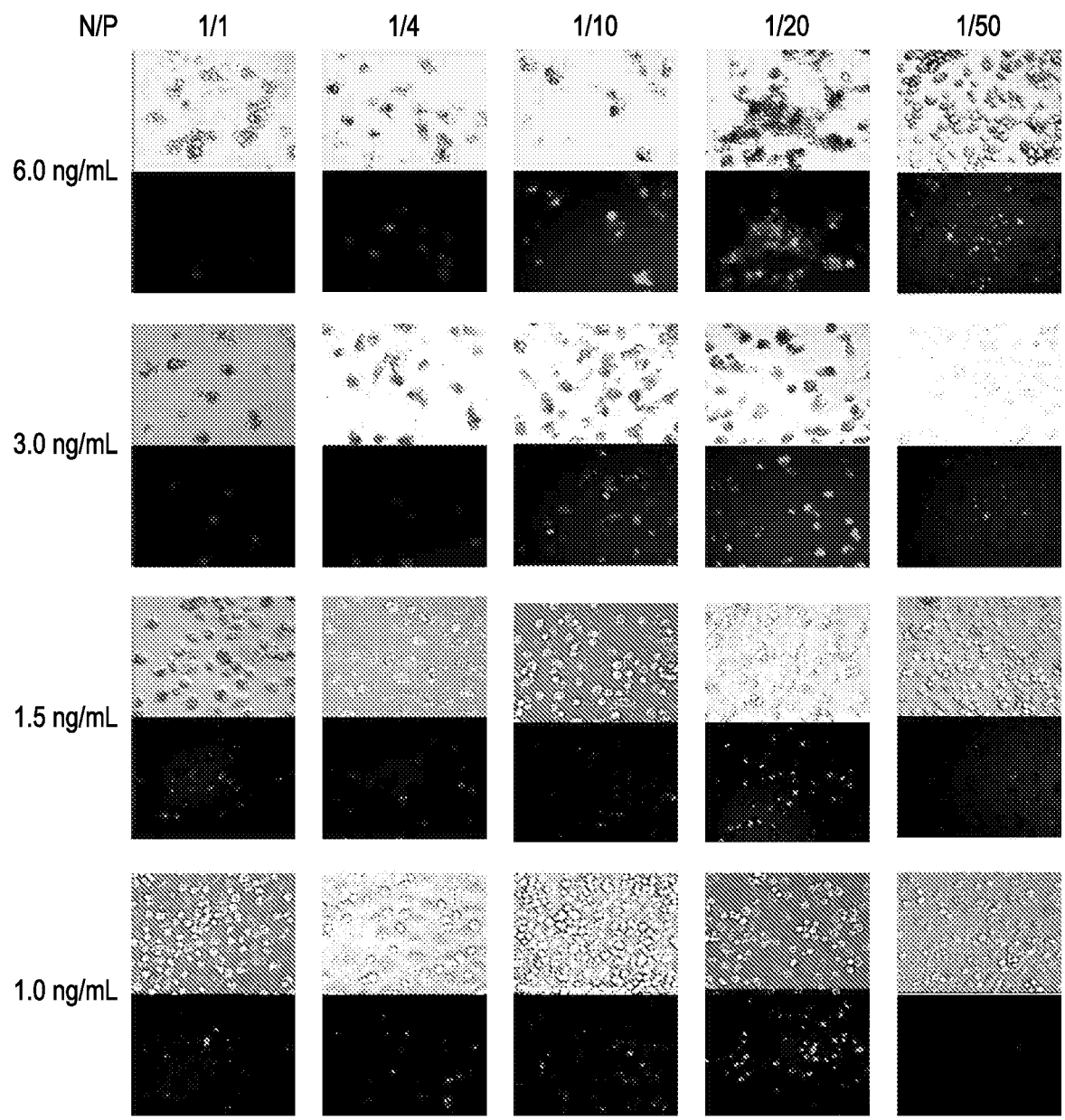
FIG. 3 shows microscopy images of human MDM were transfected by NDNA-NPs at N/P ratio of 1/1, 1/4, 1/10, 1/20, and 1/50 with the various concentrations of NDA-NPs. The GFP-IL4$^+$ human MDM (green) indicated highest transfection in DNA-NPs at N/P ratio of 1/20.
Figure 4A:
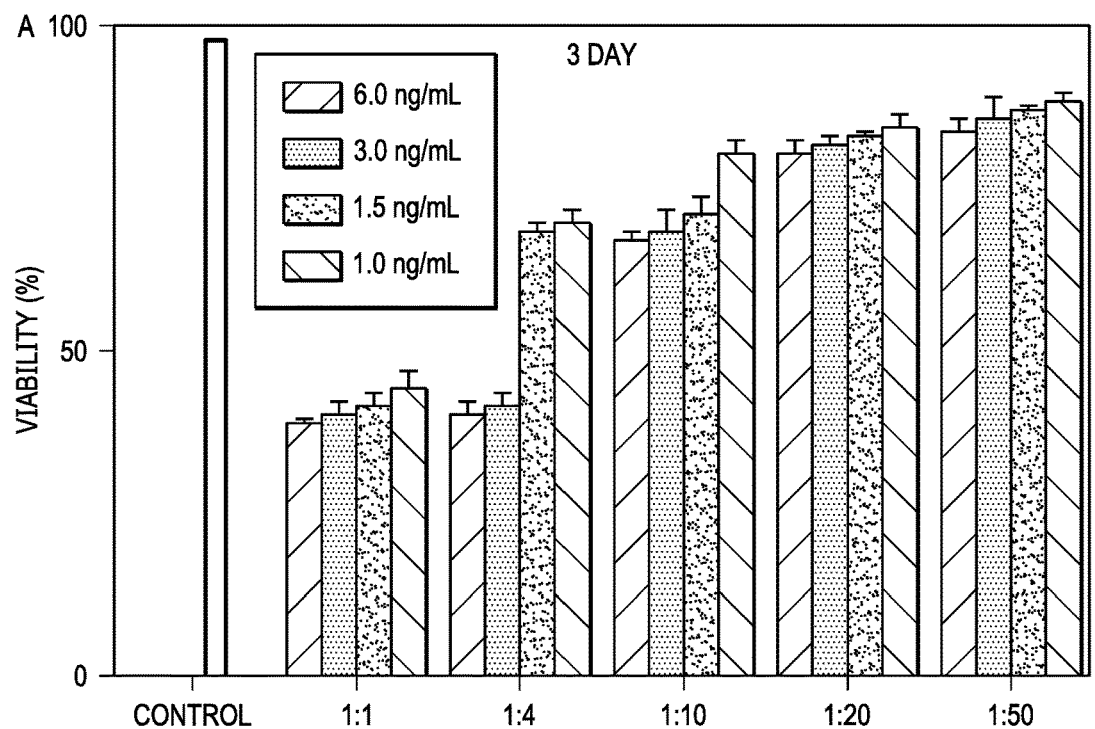
FIGS. 4A to 4F show the transfection and cell stabilities. Cell viability and GFP-IL4 transfection was detected in human MDM at day 3 and 5 with the various N/P ratio and concentration of DNA-NPs. The effect of N/P ratio on the viability of MDM in FIG. 4A and FIG. 4B. The percentage of GFP-IL4$^+$ MDM exhibited the elevation of transfection when increase of DNA loading (FIG. 4C). The transfected MDM secreting of IL-4 into medium were determined at day 5 by ELISA assay (FIG. 4D). The time-dependent transfection profiles were tested by the GFP fluorescent intensity (FIG. 4E). When fixed the DNA-NPs at N/P ratio of 1/20, the secretion of IL4 from transfected MDM showed time-dependent increased trend (FIG. 4F).
Figure 4B:
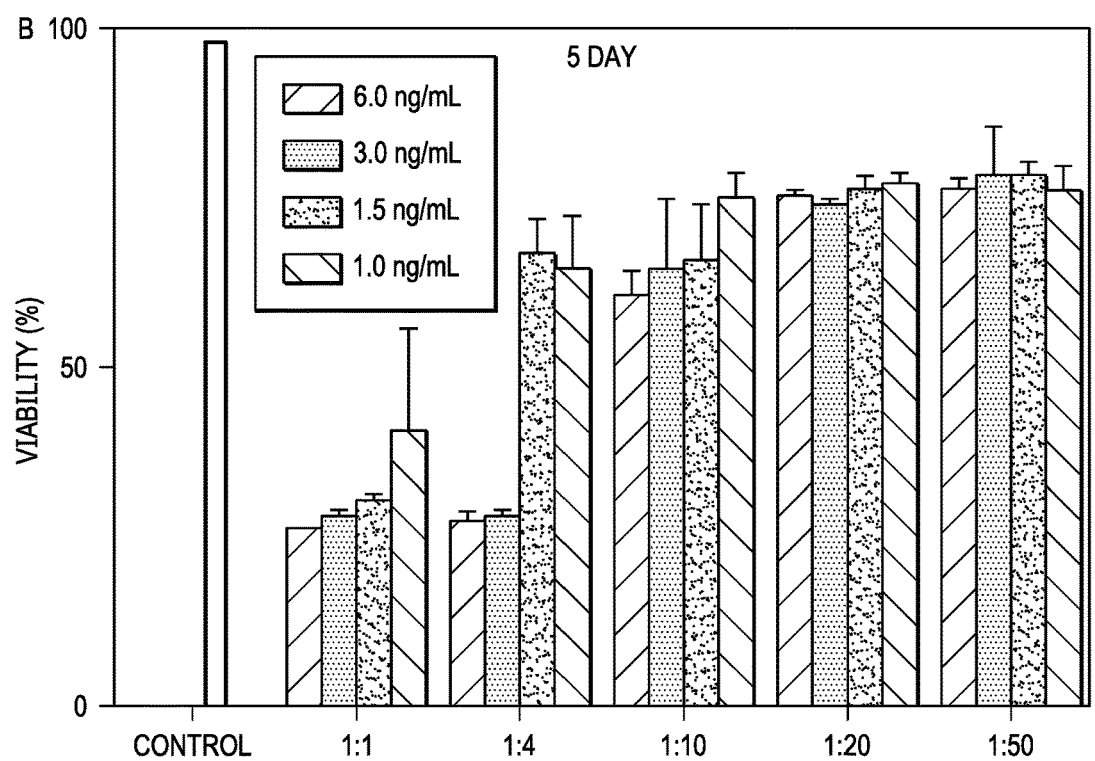
Figure 4C:
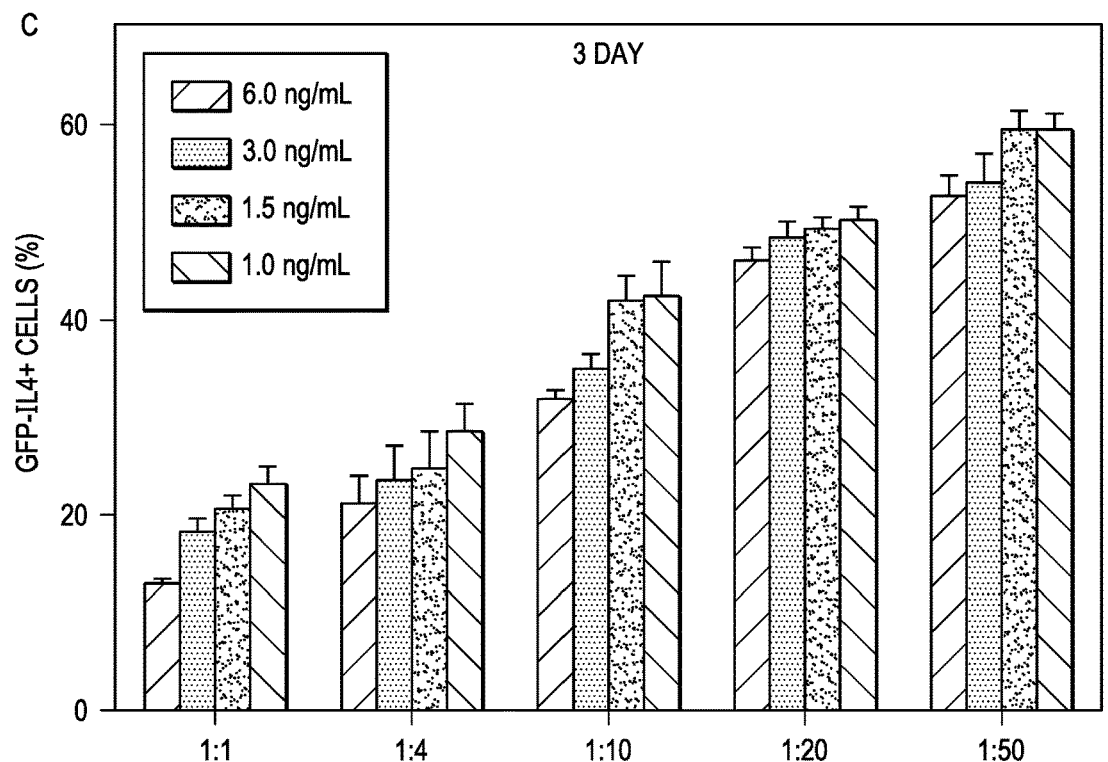
Figure 4D:
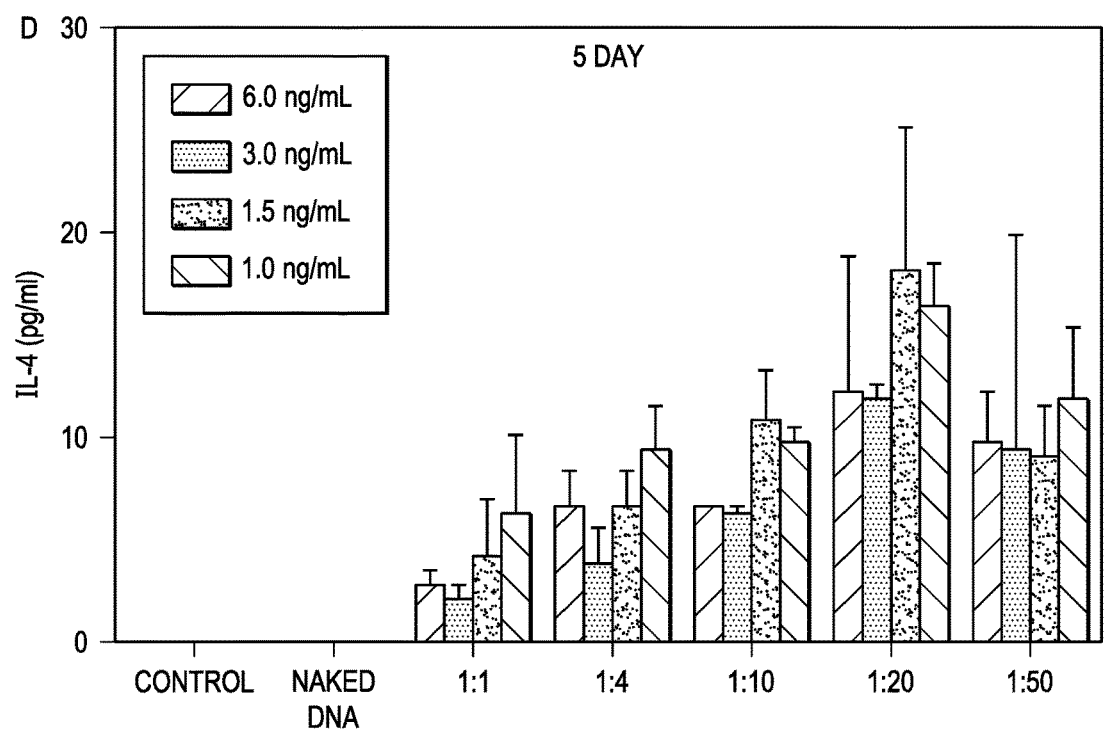

DNA-NPs delivery to MDM. DNA-NPs effectively delivered plasmid of GFP-IL4 into human blood monocytes derived macrophages (MDM). The GFP-IL4 expression was detected at various conditions of 5 days after transfection (FIG. 3). GFP-IL4 expression occurred in all the condition even though the cell viability differed from the conditions. Inside the ratio of the NPs and DNA, higher expression could observe up to 1:20. Also, the concentration of DNA-NPs and the N/P ratio of DNA loading affected MDM viability (FIG. 4A and FIG. 4B) and transfection efficacy (FIG. 4C and FIG. 4D). In detail of cell viability, the ratio of complexes of NPs and DNA (NPs:DNA) above 1:10 showed higher cell viability in post 3 and 5 days transfection. On average, higher cell viability reveled was shown at NPs-DNA complexes concentrations of 1.5 and 1.0 ng/mL. In case of the transfection efficacy, the higher ratio of the complexes of NPs and DNA accompany with lower concentration of complexes because higher concentration of NPs induced high toxicity. A higher transfection efficacy of around <50% was achieved at above of 1:20 and 1:50 of the ratio of NPs-DNA complexes and at the concentrations of the NPs-DNA complexes at 1.5 and 1.0 ng/mL. The result of IL-4 secretion supported the result of the transfection efficacy (FIG. 3). It was observed that post 5 days transfection, NPs-DNA complexes at 1:20 and 1.5 ng/mL had IL-4 secretion significantly increased in comparison to the control. These results indicated that this condition could induce the expression of IL-4 in cells, leading to high transfection. By all accounts, the inventors selected the condition of NPs:DNA at 1:20 and 1.5 ng/mL of DNA-NPs complexes in this study. NPs-DNA complexes shifted fluorescence intensity profiles to the higher position, indicating that the transfection was significantly enhanced due to the well cellular uptake. Moreover, it reflects that the effectiveness of gene transfer is governed by the physicochemical properties of gene carrier and the overall transfection performance relates with the condition of complexes. Among the 5 different ratio conditions of NPs:DNA at 1.5 ng/mL of complexes, the ratio of NPs:DNA of 1:20 exhibited the most significant transfection with efficiency of 46.4%, in agreement with the result of the analysis of the microscopy (FIG. 3).

Figure 4E:
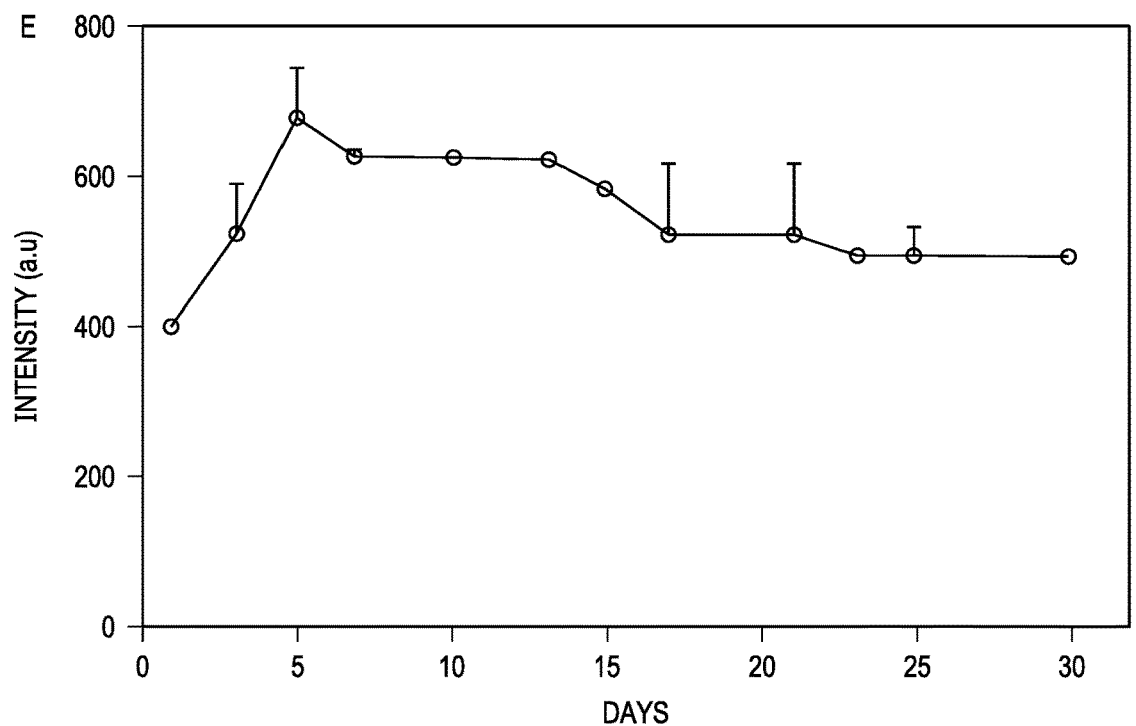
Figure 4F:
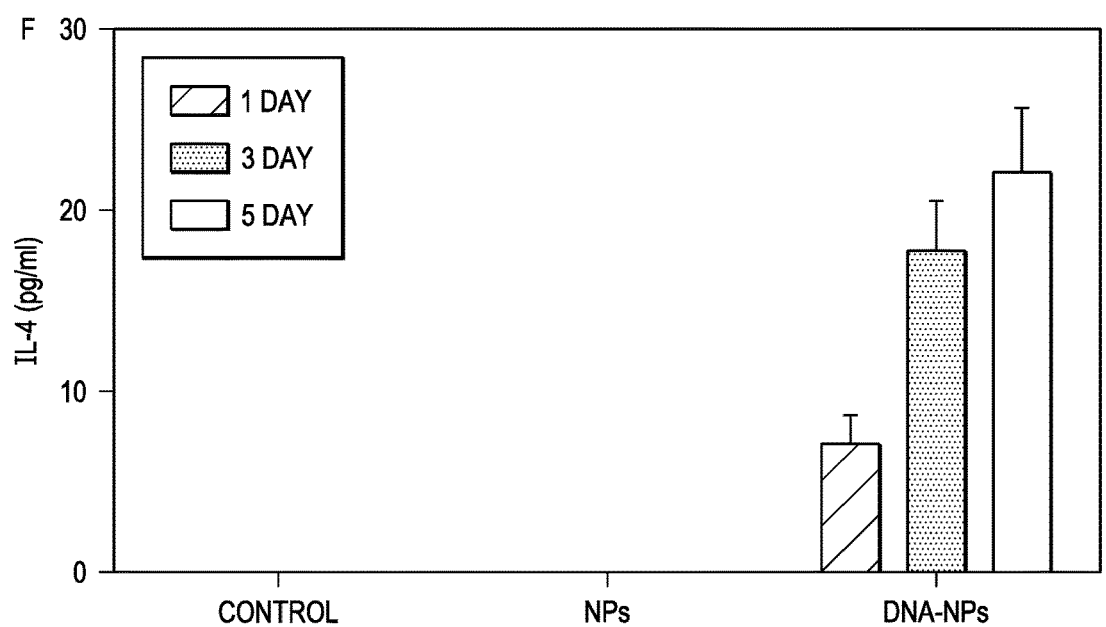

DNA transfection and MDM viability. The MDM viability was determined at day 3 and 5 after transfection with different concentration and N/P ratio of DNA-NPs (FIG. 4A and FIG. 4B). The quantity result of GFP-IL4+ MDM was shown in FIG. 4C. The transfected MDM secretion of IL-4 protein into the culture medium was analyzed by ELISA assay. With 5 days of transfection at different concentration, the highest level of IL4 protein in MDM culture medium was detected in N/P 1/20 ratio (FIG. 4D). Next, the inventors examined the long-lasting GFP-IL-4 expression up to 30 days (FIG. 4E). The results indicated that the intensity of GFP-IL4 expression revealed maximum level at day 5 and then continued expression with slight decreases to day 30. To study the time-dependent IL-4 secretion from transfected MDM, an ELISA assay was used to compare the concentration of IL-4 protein in medium in MDM, NPs treated MDM and DNA-NPs transfected MDM at day 1, 3, and 5 (FIG. 4F). It is worthwhile the IL-4 expression induced the effective delivery efficacy of DNA-NPs. Based on these results, the inventors inferred that the obtained NPs successfully delivered the DNA for gene expression and the expression saturated in post 5 days transfection.

Figure 5A:
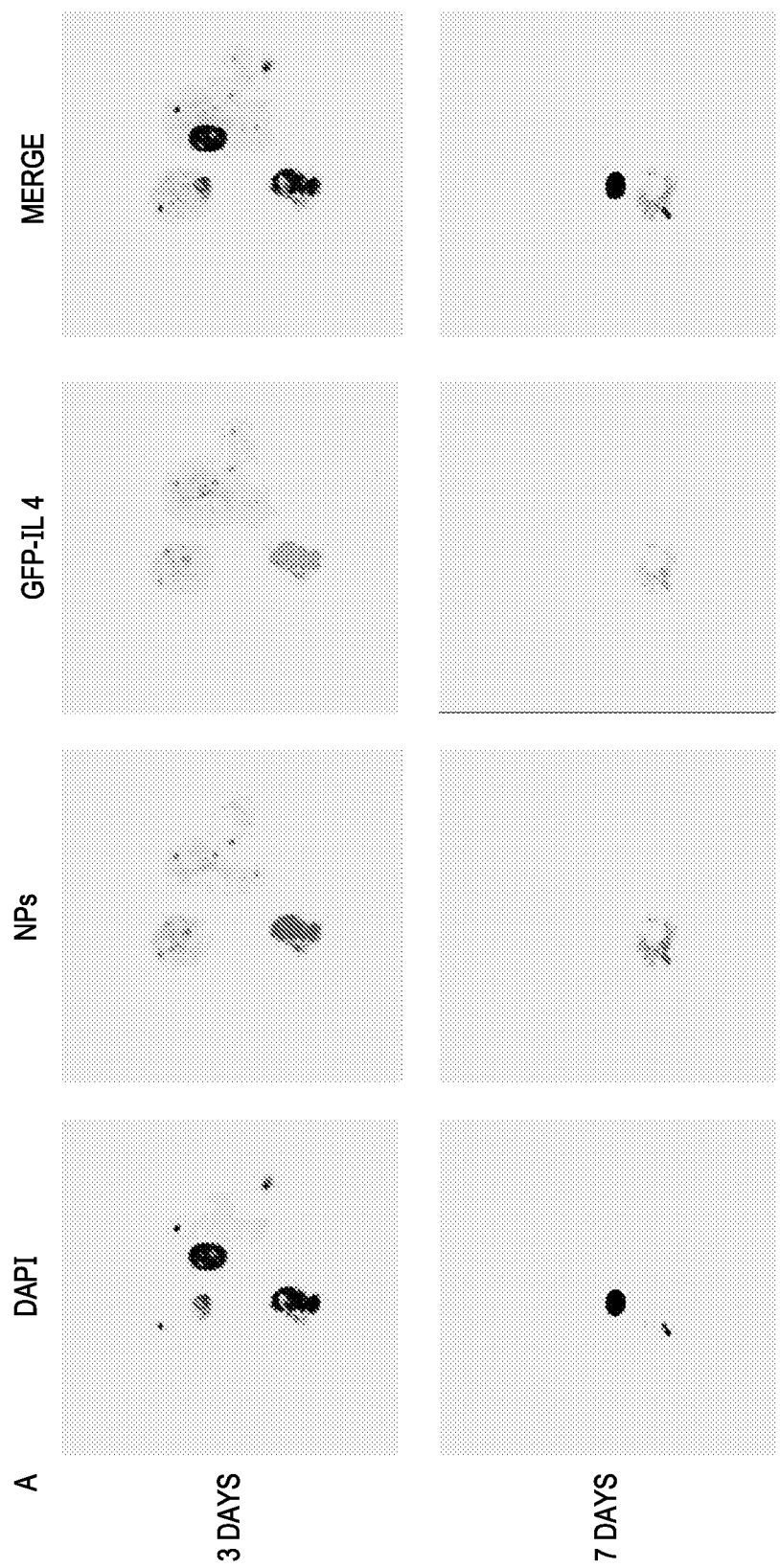
FIGS. 5A and 5B show the DNA-NPs intracellular distribution and GFP-IL-4 expression.
Figure 5B:
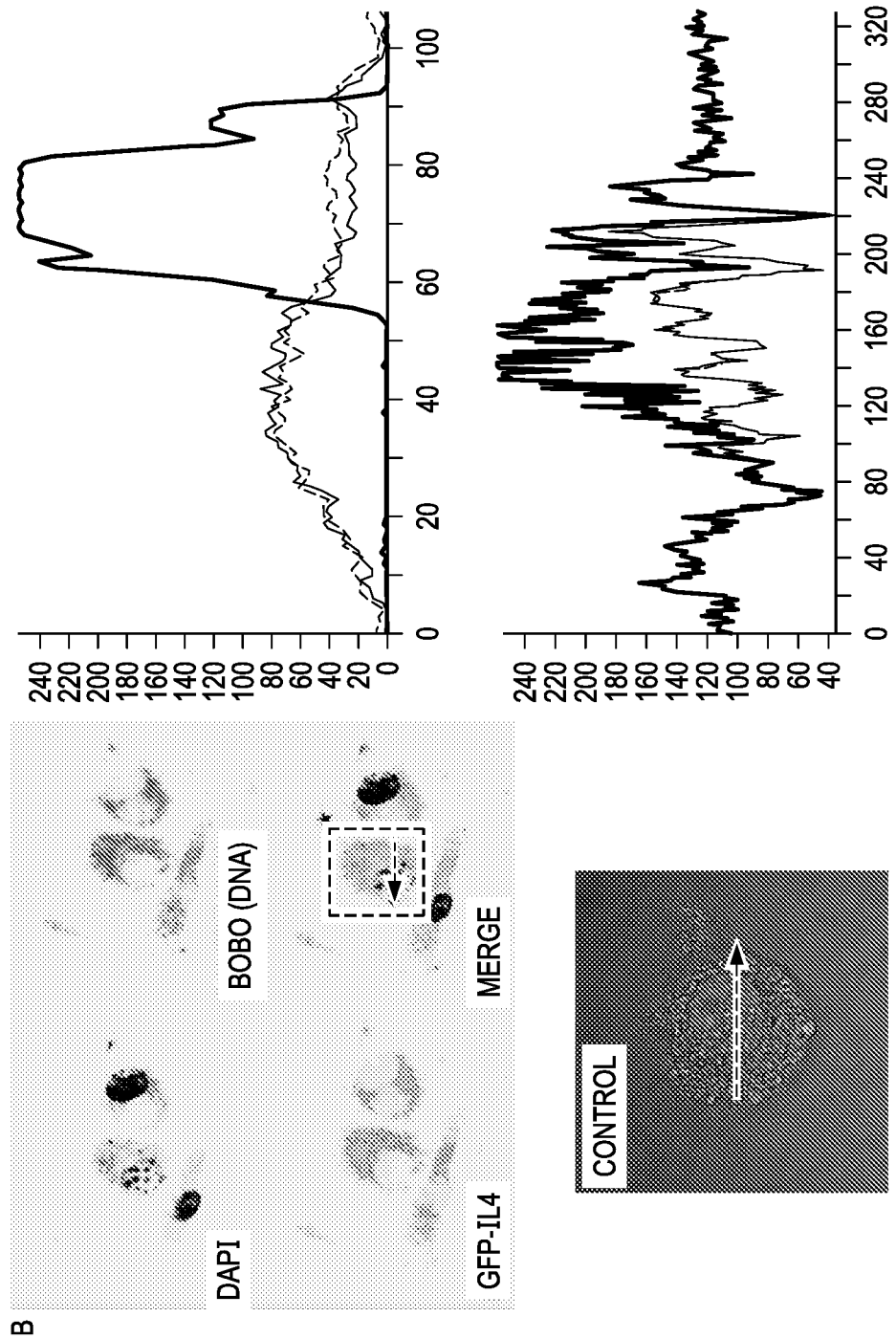

MDM uptake of DNA-NPs. For delivery systems, cellular uptake behavior reflects the delivery efficiency and the bioavailability of the carrier. From this reason, the internalization of the DNA-NPs complexes was studied. MDM were effectively taken NPs and expression of GFP-IL4. NPs packaged with BOBO-1 (red) labeled GFP-IL4 DNA was used to investigate MDM uptake and transfection. For 3 days after transfection, the images of microscopy revealed that the DNA (FIG. 5A, red) were mainly localized in the cell nucleus. More detailed information on the behavior of cell uptake was shown in FIG. 4B. Confocal images showed that higher level of GFP-IL4 expression (FIG. 5B, green) co-localized with YOYO-1 labeled DNA (FIG. 5B, red). Multiple fluorescence signals analysis of section across nuclei of MDM indicated that GFP-IL4 was mainly expressed in cytoplasm (FIG. 5B, upper panel) as compared to control signal map (FIG. 5B, lower panel). In addition, IL-4 expression was in the same location as DNA, illustrating as yellow (FIG. 5B), considering DNA delivery sites of nucleus and cytosol. The surface charge plays a key role in the uptake of NPs, which demonstrated that positively charged NPs are more effective in uptake than negatively charged one. Since the cell membrane is generally negatively charged, highly positive charged NPs might be expected to interact electrostatically with the plasma membrane, thereby increasing the chance of cellular uptake via adsorptive endocytosis[64,67]. On the basis of these concepts, the inventors assumed that surface charge highly affect the cellular uptake, and positive charged NPs promote the internalization due to the preference to contact with the negatively charged cell surface via electrostatic interaction. This behavior is able to expect favorable efficacy in most therapy cases because positively charged NPs can break through cell membrane barrier quickly and effectively, resulting in the increase of the drug concentration at the lesion site. In this contribution, the obtained NPs and DNA-NPs, which were highly positive charged as 55.1, and 52.2 mV, respectively.

Figure 6:
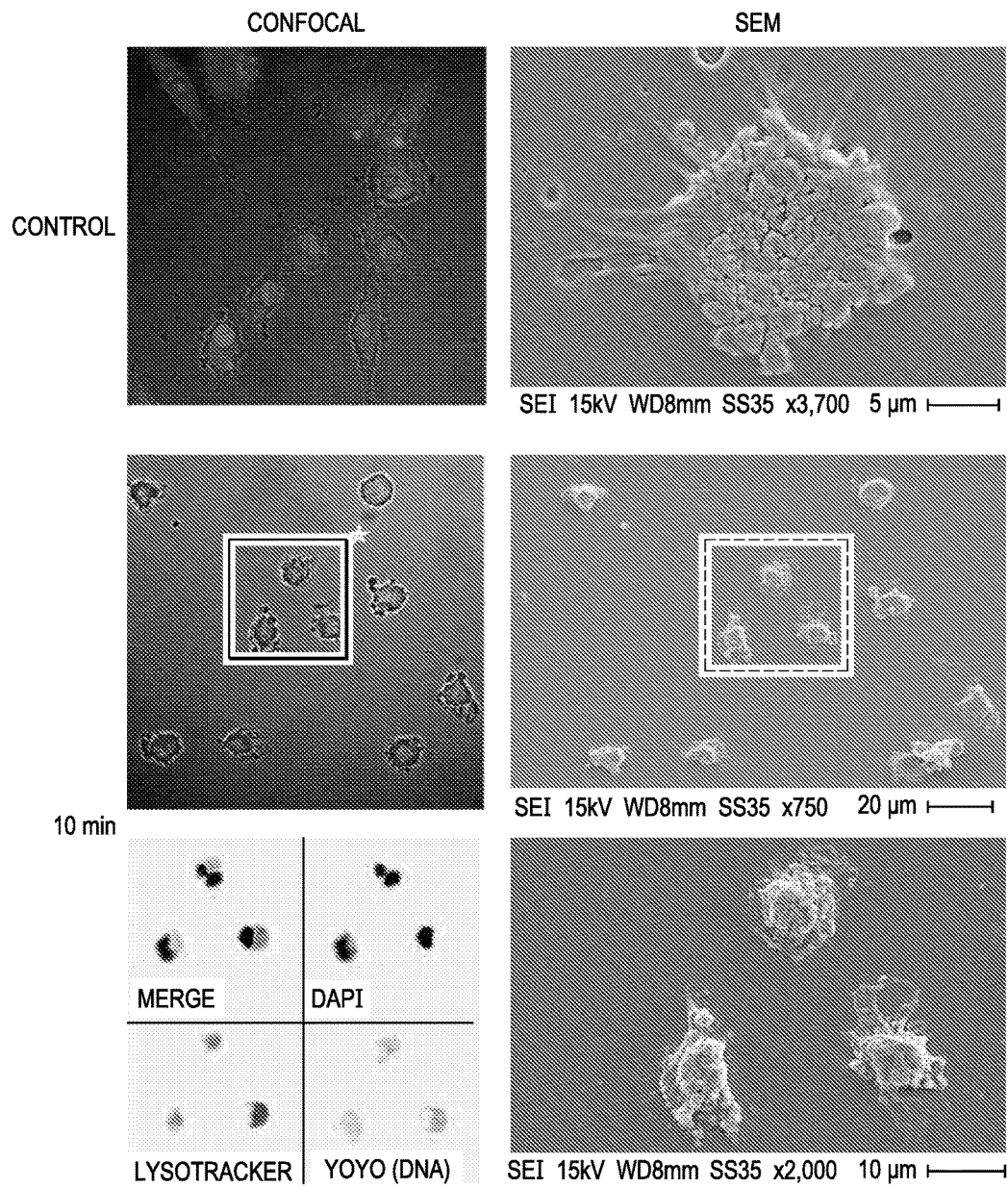
FIG. 6 shows a study of intracellular trafficking and localization of DNA-NPs. Co-imaging analysis by Confocal and SEM were obtained from MDM (control) and DNA-NPs treated cultures at 10 min. The confocal images were illustrated DAPI stained MDM nuclei (blue), LysoTracker labeled lysosome (red), and YOYO-1 labeled DNA (green). The magnification of confocal image is 100×.

Dynamic DNA-NPs intracellular localization. For high performance biological applications, the final subcellular location of NPs is a key factor besides the behavior of the cell uptake. For example in drug delivery, since many drug targets are localized to subcellular compartments such as the cytosol, endosomes, lysosomes, and the nucleus, the intracellular behavior might improve the efficacy. Co-imaging analysis by confocal and SEM further evaluated DNA-NPs uptake and dynamic DNA subcellular localization. The SEM images revealed the activation morphology of MDM (FIG. 6). The intracellular DNA trafficking was examined by confocal microscopy. Green fluorescence of YOYO-1 was used to label DNA for tracking DNA-NPs and the red LysoTracker was used to stain lysosomes. The nuclei of MDM was observed by DAPI staining. Notably, MDM uptake of DNA-NPs were detected at 10 min, leading to the co-localization of DNA (FIG. 6, green) and lysosomes (FIG. 6, red) in cytoplasm of MDM.

Figure 7A:
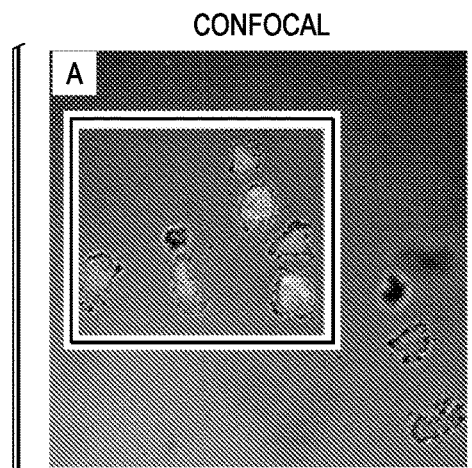
FIGS. 7A to 7H show co-imaging by confocal (FIG. 7A and FIG. 7E) and SEM (FIG. 7B and FIG. 7F) were used to analyze DNA-NPs delivery at 30 and 60 min. D and H were high magnification SEM images from FIG. 7B and FIG. 7F. The intracellular distribution YOYO-1 labeled DNA (green) and DNA release from lysosomes (red) of MDM were used to track time-dependent subcellular location of DNA at 30 and 60 min (FIG. 7C and FIG. 7G). The MDM nuclei was stained with DAPI (blue) and magnification of confocal image is 100×.
Figure 7B:
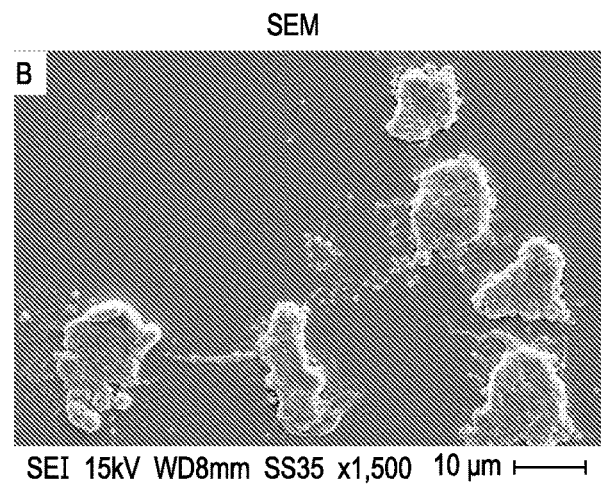
Figure 7C:
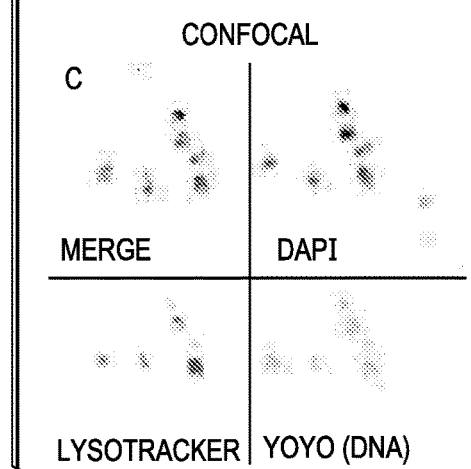
Figure 7D:
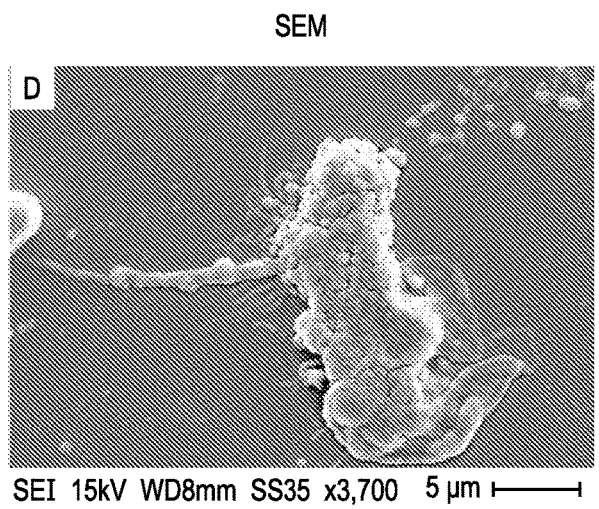
Figures 7E, 7F, 7G, 7H:
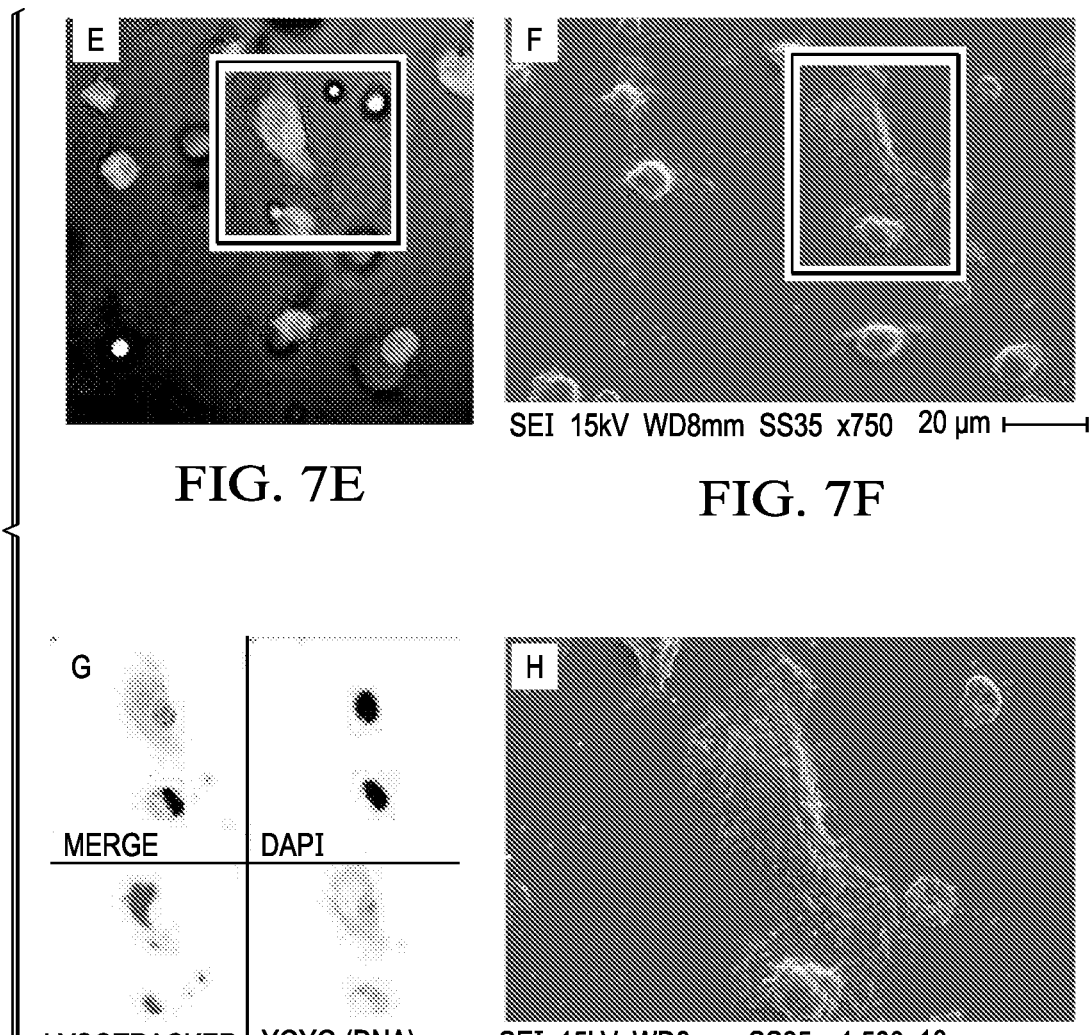

After 30 min, Confocal and SEM assays detected that the DNA was still co-localized with lysosomes in cytoplasm of MDM (FIG. 7A-FIG. 7D). However, at 60 min, the released DNA entered into nuclei, leading to mismatched fluorescence signals from DNA and lysosomes (FIG. 7E and FIG. 7G). It is a notable that DNA separated from the endosomes within 60 min, indicating the successful release of DNA from endosomes. The DNA-NPs in cytosol were apparently observed in SEM image at 30 min (FIG. 7B and FIG. 7D) and 60 min (FIG. 7F and FIG. 7H). In addition, the SEM observation gave us evidence of the activation of MDM and the subcellular transportation of DNA-NPs. Based on this study, it is worthwhile noting that the DNA-NPs obtained had a high ability of lysosome-escape without further modification. By way of explanation, and in no way a limitation of the present invention, is that the abundant positively charged NPs could trigger the concurrent influx of chloride ions to maintain charge neutrality, leading to osmotic swelling and physical rupture of the lysosomes, well-knowing as the "proton-sponge" effect[68]. In addition, this lysosome-escape ability was tested by HeLa and BMM in order to figure out the dependence of cell type (data not shown).

Figures 8A, 8B:
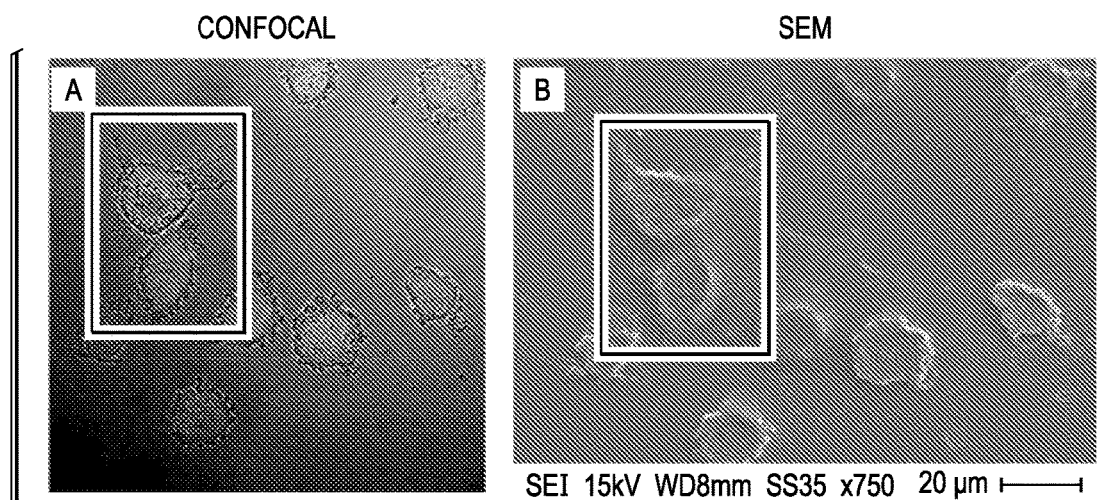
FIGS. 8A to 8H show In post transfection of 90 and 120 min, co-imaging by confocal (FIG. 8A and FIG. 8E) and SEM (FIG. 8B, FIG. 8D, FIG. 8F and FIG. 8H) was used to study the delivery efficient of DNA-NPs to transfection of MDM. YOYO-1 labeled DNA (green) were release from lysosomes (red) and entered into nuclei (blue) of MDM at 90 and 120 min (FIG. 8C and FIG. 8G).
Figures 8C, 8D:
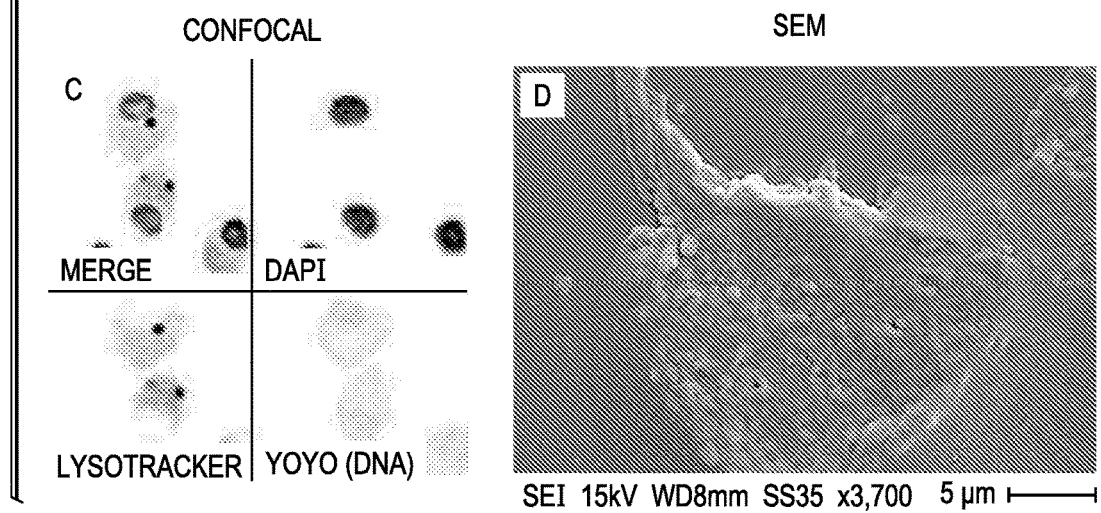
Figure 8E:
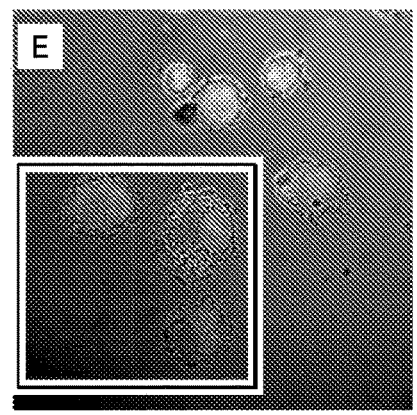
Figure 8F:
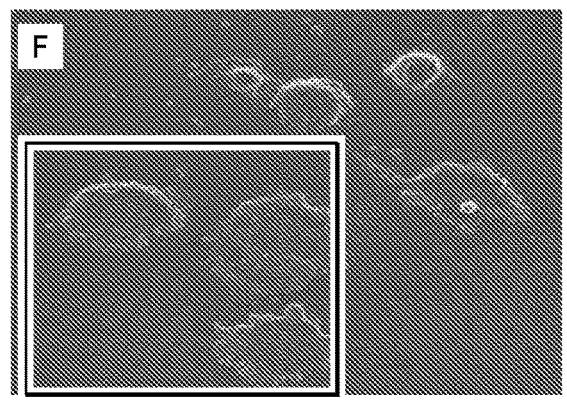
Figure 8G:
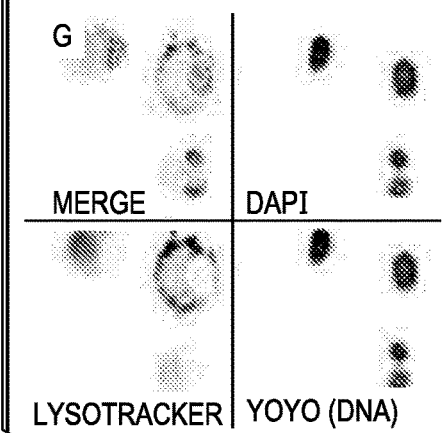
Figure 8H:
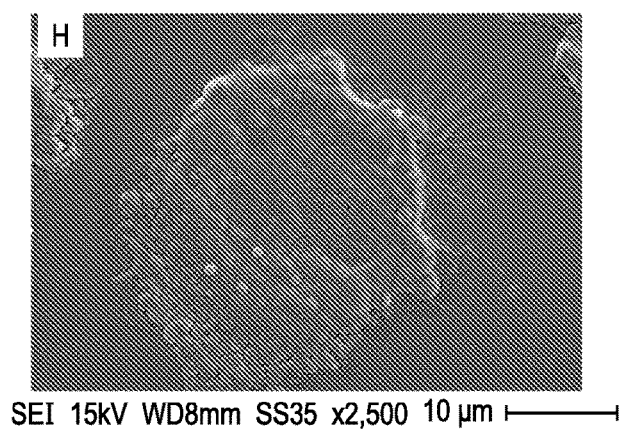

The greater expression of GFP-IL4 and the separation of DNA from endolysosome were detected at 120 min (FIG. 8E and FIG. 8G) as compared to 90 min group (FIG. 8A and FIG. 8C). The successful DNA releasing from endolysosomes plays the critical role for plasmid DNA transfection in primary macrophages. SEM images exhibited the heath and active of MDM after treated to DNA-NP up to 120 min (FIG. 8B, FIG. 8D, FIG. 8F and FIG. 8H). The significant improved viability of MDM after uptake of DNA-NPs enhanced MDM transfection. From this result, the inventors can confirm the obtained DAN-NPs had strong lysosome-escape ability for plasmid DNA delivery to transfection of MDM.

In Vivo delivery of DNA-NPs. The plasmid GFP-IL4 DNA was packaged into red fluorescence labeled NPs and administered into Balb/c mice via tail vein. The spleen was collected at day 7 post-treatment. The fresh spleen sections were directly scanned under fluorescence microscopy to determine DNA-NPs tissue distribution (FIG. 9A, red) and GFP-IL4 expression (FIG. 9A, green). Apparently, the IL-4 expression (green) and DNA-NPs (red) were observed collocated in the macrophages area of the spleen, indicating the successful macrophage targeted DNA-NPs delivery in vivo. Moreover, the inventors further investigated how IL-4 transfection regulates and polarizes splenic macrophages. NO fluorescence labeled DNA-NPs was treated to the mice for 7 days. The spleen sections were stained with antibodies to CD11b and Arginase-1. The CD11b$^+$ macrophages (FIG. 9B, red) were not observed to co-expression with GFP-IL4. In contrast, the arginase-1$^+$ M2 macrophages (FIG. 9C, red) were labeled with GFP-IL4 expression. The results indicated that the DNA-NPs effectively delivered plasmid DNA in vivo to transfected splenic macrophages for macrophages functional polarization. IL-4 as the M2 markers associated with the functionally distinct activation phenotypes. In order to define the M2 macrophages, arginase-1 has been using as a prototypic M2 marker[69]. In the mouse model, the gene included arginase-1 response to the IL-4 induced transcription factor signal transducer and its transcription is amplified by IL-4, resulting in the expression of the arginase-1 in macrophages[70].

In general, while the tissue injury and associated inflammatory milieu happen, macrophages activate two main phenotypes, termed M1 or classical activation and M2 or alternative activation[71,72]. In particular, the M2 activation is induced by fungal cells, parasites, immune complexes, complements, apoptotic cells, macrophage colony stimulating factor (MCSF), interleukin-4 (IL-4), IL-14, IL-10, tumor growth factor beta (TGF-beta)[73]. The M2 macrophages can mitigate inflammatory repose and promote wound healing, thereby attracting as anti-inflammatory, proresolving, wound healing, tissue repair, and trophic or regulatory macrophages[72,74-76]. In case of sustaining the M2-like state of tissue resident macrophages, could remove the production of inflammatory mediators, thereby approaching the treatment of metabolic disease[77,78]. For regenerative medicine, the M2 macrophages which activated from angiogenic and tissue remodeling can be used[79] for clinical application.

The inventors synthesized the gene-loaded NPs with low molecular weight PEI by vortexing modification. Vortexing significantly influenced the NPs fabrication, achieving the size of 100~300 nm as well as modification of the properties. Interestingly, up to 90 min of vortexing, the size reduced and the values of the zeta potential increased due to the enlarged surface area. The inventors inferred that various sizes and zeta potentials can be synthesized by fine-tuning the vortexing time, therefore the vortexing treatment time is one of the important factors to set the nanostructures. Based on this information, the inventors systematically investigated the behavior of the NPs including biocompatibility, cellular uptake efficiency, and intracellular trafficking in human cells. The plasma loaded NPs were quickly taken by human cells and the gene expressed in the culture under the various concentrations of the DNA-NPs complexes and the ratios of DNA to NPs. Among them, 1.5 ng/ml of complexes were made with a ratio of DNA to NPs at 1:20 showed high gene expression and cell viability. By way of explanation, and in no way a limitation of the present invention, these complexes may be internalized more effectively because cationic complexes appeared to cause plasma-membrane disruption based on the electrostatic react. These behaviors lead to the penetration of complexes, which might be attributed to the lysosome-escape ability and the electrostatic interaction between the negatively charged nucleus and the positively charged NPs. Therefore, highly positive charged NPs of the present will effectively interact with the cell intestinal epithelium, with reduced toxicity, and show an increase in cell uptake and cell transportation.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least $\pm 1$, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (0, or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Choi, Y. S., Lee, M. Y., David, A. E. & Park, Y. S. Nanoparticles for gene delivery: therapeutic and toxic effects. Mol Cell Toxicol 10, 1-8, doi:10.1007/s13273-014-0001-3 (2014).
2. Chen, J. et al. Polylysine-modified polyethylenimines as siRNA carriers for effective tumor treatment. Chinese J Polym Sci 33, 830-837, doi:10.1007/s10118-015-1632-0 (2015).
3. Dizaj, S. M., Jafari, S. & Khosroushahi, A. Y. A sight on the current nanoparticle-based gene delivery vectors. Nanoscale Res Lett 9, doi:Artn 252 10.1186/1556-276x-9-252 (2014).

4. Liu, Y. R. et al. Enhancing gene delivery of adeno-associated viruses by cell-permeable peptides. Mol Ther-Meth Clin D 1, doi:Unsp 12 10.1038/Mtm.2013.12 (2014).
5. Davis, M. E. et al. Evidence of RNAi in humans from systemically administered siRNA via targeted nanoparticles. Nature 464, 1067-U1140, doi:10.1038/nature08956 (2010).
6. Lachelt, U. & Wagner, E. Nucleic Acid Therapeutics Using Polyplexes: A Journey of 50 Years (and Beyond). Chem Rev 115, 11043-11078, doi:10.1021/cr5006793 (2015).
7. Rapti, K., Chaanine, A. H. & Hajjar, R. J. Targeted Gene Therapy for the Treatment of Heart Failure. Can J Cardiol 27, 265-283, doi:10.1016/j.cjca.2011.02.005 (2011).
8. Ando, M. et al. Prevention of adverse events of interferon gamma gene therapy by gene delivery of interferon gamma-heparin-binding domain fusion protein in mice. Mol Ther-Meth Clin D 1, doi:Unsp 14023 10.1038/Mtm.2014.23 (2014).
9. Chen, J. et al. Charge-conversional zwitterionic copolymer as pH-sensitive shielding system for effective tumor treatment. Acta biomaterialia 26, 45-53, doi:10.1016/j.actbio.2015.08.018 (2015).
10. Yin, H. et al. Non-viral vectors for gene-based therapy. Nat Rev Genet 15, 541-555, doi:10.1038/nrg3763 (2014).
11. Castanotto, D. & Rossi, J. J. The promises and pitfalls of RNA-interference-based therapeutics. Nature 457, 426-433, doi:10.1038/nature07758 (2009).
12. Lee, H. et al. Molecularly self-assembled nucleic acid nanoparticles for targeted in vivo siRNA delivery. Nat Nanotechnol 7, 389-393, doi:10.1038/Nnano.2012.73 (2012).
13. Miele, E. et al. Nanoparticle-based delivery of small interfering RNA: challenges for cancer therapy. International journal of nanomedicine 7, 3637-3657, doi:10.2147/Ijn.S23696 (2012).
14. Lee, Y. S. & Kim, S. W. Bioreducible polymers for therapeutic gene delivery. Journal of Controlled Release 190, 424-439, doi:10.1016/j.jconrel.2014.04.012 (2014).
15. Godbey, W. T., Wu, K. K. & Mikos, A. G. Poly(ethylenimine) and its role in gene delivery. Journal of Controlled Release 60, 149-160, doi:http://dx.doi.org/10.1016/S0168-3659(99)00090-5 (1999).
16. Boussif, O. et al. A versatile vector for gene and oligonucleotide transfer into cells in culture and in vivo: polyethylenimine. Proc. Natl. Acad. Sci. USA 92, 7297-7301 (1995).
17. Coll, J.-L. et al. In Vivo Delivery to Tumors of DNA Complexed with Linear Polyethylenimine. Human Gene Therapy 10, 1659-1666, doi:10.1089/10430349950017662 (1999).
18. Wightman, L. et al. Different behavior of branched and linear polyethylenimine for gene delivery in vitro and in vivo. The Journal of Gene Medicine 3, 362-372, doi:10.1002/jgm.187 (2001).
19. Mimi, H., Ho, K. M., Siu, Y. S., Wu, A. & Li, P. Polyethyleneimine-Based Core-Shell Nanogels: A Promising siRNA Carrier for Argininosuccinate Synthetase mRNA Knockdown in HeLa Cells. J. Control. Release 158, 123-130, doi:http://dx.doi.org/10.1016/j.jconrel.2011.10.035 (2012).
20. Yao, H., Ng, S.-M. S., Tang, G.-P. & Lin, M. C. Development of a Novel Low Toxicity and High Efficiency PEI-Based Nanopolymer for Gene Delivery In Vitro and In Vivo. Molecular Therapy 17, S64-S64 (2009).
21. Lungwitz, U., Breunig, M., Blunk, T. & Göpferich, A. Polyethylenimine-based non-viral gene delivery systems. European Journal of Pharmaceutics and Biopharmaceutics 60, 247-266, doi:http://dx.doi.org/10.1016/j.ejpb.2004.11.011 (2005).
22. Yamada, H., Loretz, B. & Lehr, C.-M. Design of Starch-graft-PEI Polymers: An Effective and Biodegradable Gene Delivery Platform. Biomacromolecules 15, 1753-1761, doi:10.1021/bm500128k (2014).
23. Moghimi, S. M. et al. A two-stage poly(ethylenimine)-mediated cytotoxicity: implications for gene transfer/therapy. Mol. Ther. 11, 990-995, doi:http://www.nature.com/mt/journal/v11/n6/suppinfo/mt2005120s1.html (2005).
24. Zintchenko, A., Philipp, A., Dehshahri, A. & Wagner, E. Simple modifications of branched PEI lead to highly efficient siRNA carriers with low toxicity. Bioconjugate Chemistry 19, 1448-1455, doi:10.1021/bc800065f (2008).
25. Fischer, D., Li, Y., Ahlemeyer, B., Krieglstein, J. & Kissel, T. In vitro cytotoxicity testing of polycations: influence of polymer structure on cell viability and hemolysis. Biomaterials 24, 1121-1131, doi:http://dx.doi.org/10.1016/S0142-9612(02)00445-3 (2003).
26. Gao, J.-Q. et al. Gene-carried chitosan-linked-PEI induced high gene transfection efficiency with low toxicity and significant tumor-suppressive activity. International Journal of Pharmaceutics 387, 286-294, doi:10.1016/j.ijpharm.2009.12.033 (2010).
27. Kim, Y. H. et al. Polyethylenimine with acid-labile linkages as a biodegradable gene carrier. Journal of Controlled Release 103, 209-219, doi:http://dx.doi.org/10.1016/j.jconrel.2004.11.008 (2005).
28. Beyerle, A., Irmler, M., Beckers, J., Kissel, T. & Stoeger, T. Toxicity Pathway Focused Gene Expression Profiling of PEI-Based Polymers for Pulmonary Applications. Molecular Pharmaceutics 7, 727-737, doi:10.1021/mp900278x (2010).
29. Dong, W. et al. Cross-linked Polyethylenimine as Potential DNA Vector for Gene Delivery with High Efficiency and Low Cytotoxicity. Acta Biochimica et Biophysica Sinica 38, 780-787, doi:10.1111/j.1745-7270.2006.00220.x (2006).
30. Forrest, M. L., Koerber, J. T. & Pack, D. W. A Degradable Polyethylenimine Derivative with Low Toxicity for Highly Efficient Gene Delivery. Bioconjugate Chemistry 14, 934-940, doi:10.1021/bc034014g (2003).
31. Xun, M.-M. et al. Low molecular weight PEI-based polycationic gene vectors via Michael addition polymerization with improved serum-tolerance. Polymer 65, 45-54, doi:http://dx.doi.org/10.1016/j.polymer.2015.03.070 (2015).
32. von Harpe, A., Petersen, H., Li, Y. X. & Kissel, T. Characterization of commercially available and synthesized polyethylenimines for gene delivery. Journal of Controlled Release 69, 309-322, doi:Doi 10.1016/S0168-3659(00)00317-5 (2000).
33. Kircheis, R., Wightman, L. & Wagner, E. Design and gene delivery activity of modified polyethylenimines. Adv Drug Deliver Rev 53, 341-358, doi:Doi 10.1016/S0169-409x(01)00202-2 (2001).
34. Gautam, A., Densmore, C. L., Xu, B. & Waldrep, J. C. Enhanced gene expression in mouse lung after PEI-DNA aerosol delivery. Mol Ther 2, 63-70, doi:DOI 10.1006/mthe.2000.0087 (2000).
35. Gautam, A., Densmore, C. L., Golunski, E., Xu, B. & Waldrep, J. C. Transgene expression in mouse airway 35. epithelium by aerosol gene therapy with PEI-DNA complexes. Mol Ther 3, 551-556, doi:10.1006/mthe.2001.0300 (2001).
36. Gautam, A., Densmore, C. L. & Waldrep, J. C. Pulmonary cytokine responses associated with PEI-DNA aerosol gene therapy. Gene Ther 8, 254-257, doi:DOI 10.1038/sj.gt.3301369 (2001).
37. Densmore, C. L. et al. Aerosol delivery of robust polyethyleneimine-DNA complexes for gene therapy and genetic immunization. Mol Ther 1, 180-188, doi:10.1006/mthe.1999.0021 (2000).
38. Liu, Y. T., Pan, J. & Feng, S. S. Nanoparticles of lipid monolayer shell and biodegradable polymer core for controlled release of paclitaxel: Effects of surfactants on particles size, characteristics and in vitro performance. International Journal of Pharmaceutics 395, 243-250, doi:10.1016/j.ijpharm.2010.05.008 (2010).
39. Freitas, S., Merkle, H. P. & Gander, B. Microencapsulation by solvent extraction/evaporation: reviewing the state of the art of microsphere preparation process technology. Journal of Controlled Release 102, 313-332, doi:10.1016/j.jconrel.2004.10.015 (2005).
40. Xiao, J. et al. Low Molecular Weight Polyethylenimine-graft-Tween 85 for Effective Gene Delivery: Synthesis and in Vitro Characteristics. Bioconjugate Chem. 23, 222-231, doi:10.1021/bc200504v (2012).
41. Bivas-Benita, M., Romeijn, S., Junginger, H. E. & Borchard, G. PLGA-PEI nanoparticles for gene delivery to pulmonary epithelium. European Journal of Pharmaceutics and Biopharmaceutics 58, 1-6, doi:10.1016/j.ejpb.2004.03.008 (2004).
42. Cao, Q., Zheng, D., Wang, Y. P. & Harris, D. C. H. Macrophages and Dendritic Cells for Treating Kidney Disease. Nephron Exp Nephrol 117, E47-E52, doi:10.1159/000320595 (2011).
43. Chavez-Galan, L., Olleros, M. L., Vesin, D. & Garcia, I. Much more than M1 and M2 macrophages, there are also CD169(+) and TCR+ macrophages. Front Immunol 6, doi:Unsp 263 10.3389/Fimmu.2015.00263 (2015).
44. Gordon, S. Alternative activation of macrophages. Nat Rev Immunol 3, 23-35, doi:10.1038/nri978 (2003).
45. Cassol, E., Cassetta, L., Alfano, M. & Poli, G. Macrophage polarization and HIV-1 infection. J Leukocyte Biol 87, 599-608, doi:10.1189/jlb.1009673 (2010).
46. Medzhitov, R. Origin and physiological roles of inflammation. Nature 454, 428-435, doi:10.1038/nature07201 (2008).
47. Booth, C., Carmo, M. & Gaspar, H. B. Gene Therapy for Haemophagocytic Lymphohistiocytosis. Curr Gene Ther 14, 437-446 (2014).
48. Shukla, S. K. et al. Cytotoxic and radioprotective effects of *Podophyllum hexandrum*. Environmental toxicology and pharmacology 22, 113-120, doi:10.1016/j.etap.2006.01.001 (2006).
49. Chuang, C. C. & Chang, C. W. Complexation of bioreducible cationic polymers with gold nanoparticles for improving stability in serum and application on nonviral gene delivery. ACS Appl Mater Interfaces 7, 7724-7731, doi:10.1021/acsami.5b00732 (2015).
50. Gao, D. et al. Ultrasound-Triggered Phase-Transition Cationic Nanodroplets for Enhanced Gene Delivery. ACS Appl Mater Interfaces 7, 13524-13537, doi:10.1021/acsami.5b02832 (2015).
51. Zhang, Q. F. et al. Ring-opening polymerization for hyperbranched polycationic gene delivery vectors with excellent serum tolerance. ACS Appl Mater Interfaces 6, 15733-15742, doi:10.1021/am5046185 (2014).
52. Feng, X. L., Tang, Y. L., Duan, X. R., Liu, L. B. & Wang, S. Lipid-modified conjugated polymer nanoparticles for cell imaging and transfection. J Mater Chem 20, 1312-1316, doi:10.1039/b915112e (2010).
53. Zhi, D. et al. The Headgroup Evolution of Cationic Lipids for Gene Delivery. Bioconjugate Chem. 24, 487-519, doi:10.1021/bc300381s (2013).
54. Wan, D., Wang, G., Pu, H. & Jin, M. Can Nonspecific Host-Guest Interaction Lead to Highly Specific Encapsulation by a Supramolecular Nanocapsule? Macromolecules 42, 6448-6456, doi:10.1021/ma900952e (2009).
55. Wan, D., Pu, H., Jin, M., Pan, H. & Chang, Z. Enhancing the unimolecularity and control for guest release of a macromolecular nanocapsule via core engineering. React. Funct. Polym. 70, 916-922, doi:http://dx.doi.org/10.1016/j.reactfunctpolym.2010.09.002 (2010).
56. Zou, L., Zhu, W., Chen, Y. & Xi, F. Modification of side chain terminals of PEGylated molecular bottle brushes—A toolbar of molecular nanoobjects. Polymer 54, 481-484, doi:http://dx.doi.org/10.1016/j.polymer.2012.12.020 (2013).
57. Sun, T.-M. et al. Simultaneous Delivery of siRNA and Paclitaxel via a "Two-in-One" Micelleplex Promotes Synergistic Tumor Suppression. ACS Nano 5, 1483-1494, doi:10.1021/nn103349h (2011).
58. Wang, Y., Gao, S., Ye, W.-H., Yoon, H. S. & Yang, Y.-Y. Co-delivery of drugs and DNA from cationic core-shell nanoparticles self-assembled from a biodegradable copolymer. Nat. Mater. 5, 791-796, doi:http://www.nature.com/nmat/journal/v5/n10/suppinfo/nmat1737_S1.html (2006).
59. Zhu, J. et al. Amphiphilic Core-Shell Nanoparticles with Poly(ethylenimine) Shells as Potential Gene Delivery Carriers. Bioconjugate Chem. 16, 139-146, doi:10.1021/bc0498951 (2005).
60. Moncada, C., Torres, V. & Israel, Y. Simple Method for the Preparation of Antigen Emulsions for Immunization. J Immunol Methods 162, 133-140, doi:Doi 10.1016/0022-1759(93)90415-4 (1993).
61. Vulliet, R. Improved technique for the preparation of water-in-oil emulsions containing protein antigens. Biotechniques 20, 797-& (1996).
62. Flies, D. B. & Chen, L. P. A simple and rapid vortex method for preparing antigen/adjuvant emulsions for immunization. J Immunol Methods 276, 239-242, doi:10.1016/S0022-1759(03)00081-4 (2003).
63. Rojanasakul, Y. et al. The Transport Barrier of Epithelia—a Comparative-Study on Membrane-Permeability and Charge Selectivity in the Rabbit. Pharmaceutical research 9, 1029-1034, doi:Doi 10.1023/A:1015802427428 (1992).
64. Harush-Frenkel, O., Rozentur, E., Benita, S. & Altschuler, Y. Surface charge of nanoparticles determines their endocytic and transcytotic pathway in polarized MDCK cells. Biomacromolecules 9, 435-443, doi:10.1021/bm700535p (2008).
65. Shaw, P. J. & Jordan, E. G. The nucleolus. Annu Rev Cell Dev Bi 11, 93-121, doi:DOI 10.1146/annurev.cellbio.11.1.93 (1995).
66. Weecharangsan, W. et al. Evaluation of chitosan salts as non-viral gene vectors in CHO-Kl cells. International journal of pharmaceutics 348, 161-168, doi:10.1016/j.ijpharm.2007.07.011 (2008).
67. Rojanasakul, Y. et al. The transport barrier of epithelia: a comparative study on membrane permeability and charge selectivity in the rabbit. Pharmaceutical research 9, 1029-1034 (1992).

68. Zhang, Y. H. et al. Single-Molecule Study on Intermolecular Interaction between C-60 and Porphyrin Derivatives: Toward Understanding the Strength of the Multivalency. Langmuir: the ACS journal of surfaces and colloids 25, 6627-6632, doi:10.1021/la901360c (2009).
69. Stempin, C. C., Dulgerian, L. R., Garrido, V. V. & Cerban, F. M. Arginase in Parasitic Infections: Macrophage Activation, Immunosuppression, and Intracellular Signals. J Biomed Biotechnol, doi:Artn 683485 10.1155/2010/683485 (2010).
70. Dzik, J. M. Evolutionary roots of arginase expression and regulation. Front Immunol 5, doi:Artn 544 10.3389/Fimmu.2014.00544 (2014).
71. Martinez, F. O. & Gordon, S. The M1 and M2 paradigm of macrophage activation: time for reassessment. F1000prime reports 6, 13, doi:10.12703/P6-13 (2014).
72. Sica, A. & Mantovani, A. Macrophage plasticity and polarization: in vivo veritas. The Journal of clinical investigation 122, 787-795, doi:10.1172/JCI59643 (2012).
73. Murray, P. J. et al. Macrophage activation and polarization: nomenclature and experimental guidelines. Immunity 41, 14-20, doi:10.1016/j.immuni.2014.06.008 (2014).
74. Pollard, J. W. Trophic macrophages in development and disease. Nat Rev Immunol 9, 259-270, doi:10.1038/nri2528 (2009).
75. Ferrante, C. J. & Leibovich, S. J. Regulation of Macrophage Polarization and Wound Healing. Advances in wound care 1, 10-16, doi:10.1089/wound.2011.0307 (2012).
76. Morris, D. L., Singer, K. & Lumeng, C. N. Adipose tissue macrophages: phenotypic plasticity and diversity in lean and obese states. Current opinion in clinical nutrition and metabolic care 14, 341-346, doi:10.1097/MCO.0b013e328347970b (2011).
77. Osborn, 0. & Olefsky, J. M. The cellular and signaling networks linking the immune system and metabolism in disease. Nature medicine 18, 363-374, doi:10.1038/nm.2627 (2012).
78. Glass, C. K. & Olefsky, J. M. Inflammation and Lipid Signaling in the Etiology of Insulin Resistance. Cell Metab 15, 635-645, doi:10.1016/j.cmet.2012.04.001 (2012).
79. Rigamonti, E., Zordan, P., Sciorati, C., Rovere-Querini, P. & Brunetti, S. Macrophage Plasticity in Skeletal Muscle Repair. BioMed research international, doi:Artn 560629.

The invention claimed is:

1. A transfection complex comprising:
one or more polyethyleneimine800-EpoxyC8-22 (PEI800-C8-22) lipids complexed with one or more nucleic acids on one or more nanoparticles.

2. The complex of claim 1, wherein the PEI800-C8-22 lipid is selected from at least one of: a PEI-EpoxyC16 lipid synthesized at molar ratio of 4 to 1 PEI800 to EpoxyC8-22 to 1 to 14 PEI800 to EpoxyC8-22;
PEI800-C8-22 lipid is a PEI-EpoxyC16 lipid synthesized at molar ratio of 1 to 12 (PEI12C16);
PEI800-C8-22 lipid is a PEI-EpoxyC16 lipid synthesized at molar ratio at 1 to 8 (PEI8C16); or
PEI800-C8-22 lipid is a PEI-EpoxyC16 lipid synthesized at molar ratio at 1 to 8 (PEI8C16).

3. The complex of claim 1, wherein the PEI800 is a branched polyethyleneimine.

4. The complex of claim 1, wherein the PEI800-C8-22 lipid is at least one of a Polyethyleneimine800-EpoxyC16 (PEI-C16), PEI12C16, PEI8C16, or PEI4C16 lipid formed into a core-shell nanoparticle, or a liposome.

5. The complex of claim 1, wherein the PEI800-C8-22 is selected from at least one of a C8, C9, C10, C11, C12, C13, C14, C15, C16, C17, C18, C19, C20, C21, or C22 lipid, mixtures, or combinations thereof.

6. The complex of claim 1, wherein the nanoparticle is further defined as at least one of a biocompatible or biodegradable polymer or further comprises biodegradable polymers.

7. The complex of claim 1, wherein the nucleic acid is DNA or RNA, small interfering RNA (siRNA), messenger RNA (mRNA), single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (as-RNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA.

8. The complex of claim 1, wherein the PEI800-C8-22 lipid is an amphiphilic polyethyleneimine800 (PEI800)-EpoxyC16 (PEI-C16), PEI12C16, PEI8C16 and PEI4C16 lipids that further comprise hexadecyl tail groups, polyethylene glycol groups, low branched molecular weight PEI, or poly (lactic-co-glycolic acid) PLGA.

9. The complex of claim 1, wherein the PEI800-C8-22 lipid is at least one of an amphiphilic polyethyleneimine800 (PEI800)-EpoxyC16 (PEI-C16), PEI12C16, PEI8C16, or PEI4C16 lipid formed in nanoparticles and liposomes comprises a nucleic acid vector, a plasmid DNA, a viral DNA, a self-replicating DNA, a short hairpin RNA or small hairpin RNA (shRNA/Hairpin Vector), a small non-coding RNA (miRNA), a bifunctional shRNA, or interference RNA (RNAi).

10. The complex of claim 1, wherein the C8-22 lipid is at least one of a phosphatidylcholine, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC,), 1-palmitoyl-2-oleylphosphatidylcholine (POPC), 1-oleyl-2-palmitoyl-phosphatidylcholine (OPPC), dilauroyl-phosphatidylglycerol (DLPG), diarachidoylphosphatidyl-glycerol (DAPG), dimyristoylphosphatidylglycerol (DMPG), dipalmitoylphosphatidylglycerol (DPPG), distearoylphosphatidylglycerol (DSPG, dioleoyl-phosphatidylglycerol (DOPG), dimyristoyl phosphatidic acid (DMPA), dipalmitoyl phosphatidic acid (DPPA), distearoyl phosphatidic acid (DSPA), diarachidoylphosphatidic acid (DAPA), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), polyethyleneglycol modified dimyristoyl-phosphatidylethanolamine (DMPE-PEG), polyethyleneglycol modified dipalmitoylphosphatidylethanolamine (DPPE-PEG), polyethyleneglycol modified distearoyl phosphatidyl-ethanolamine (DSPE-PEG), polyethyleneglycol modified dioleylphosphatidyl-ethanolamine (DOPE-PEG), polyethyleneglycol modified diarachidoylphosphatidylethanolamine (DAPE-PEG), polyethyleneglycol modified dilinoleylphosphatidylethanolamine (DLPE-PEG), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP) and mixtures thereof.

11. A method of synthesis of amphiphilic polyethyleneimine800-EpoxyC8-22 comprising:
    mixing a polyethyleneimine800 (PEI800) with an EpoxyC8-22 under conditions in which a polyethyleneimine800-EpoxyC8-22 lipid is formed.

12. A method of making a transfection complex comprising:
    mixing a nanoparticle with a polyethyleneimine800-EpoxyC8-22 lipid to form a nanoparticle-lipid complex;
    and mixing the nanoparticle-lipid complex with at least one of a DNA, an RNA, a nucleic acid vector, a shRNA, miRNA, or RNAi to form the transfection complex.

13. The method of claim 12, wherein the PEI800-C8-22 lipid is selected from at least one of: a PEI-EpoxyC16 lipid synthesized at molar ratio of 4 to 1 PEI800 to EpoxyC8-22 to 1 to 14 PEI800 to EpoxyC8-22;
    PEI800-C8-22 lipid is a PEI-EpoxyC16 lipid synthesized at molar ratio of 1 to 12 (PEI12C16);
    PEI800-C8-22 lipid is a PEI-EpoxyC16 lipid synthesized at molar ratio at 1 to 8 (PEI8C16); or
    PEI800-C8-22 lipid is a PEI-EpoxyC16 lipid synthesized at molar ratio at 1 to 8 (PEI8C16).

14. The method of claim 12, wherein the PEI800 is a branched polyethyleneimine.

15. The method of claim 13, wherein the amphiphilic polyethyleneimine800 (PEI800)-EpoxyC16 (PEI-C16), PEI12C16, PEI8C16, and PEI4C16 lipids are formed into a core-shell nanoparticle, or a liposome.

16. The method of claim 12, wherein the nanoparticle-lipid complex comprise at least one of a biocompatible polymer or a biodegradable polymer or further comprises biodegradable polymers.

17. The method of claim 13, wherein the amphiphilic polyethyleneimine800 (PEI800)-EpoxyC16 (PEI-C16), PEI12C16, PEI8C16, and PEI4C16 lipids further comprise at least one of: hexadecyl tail groups, polyethylene glycol groups, or poly (lactic-co-glycolic acid) PLGA.

18. The method of claim 13, wherein the amphiphilic polyethyleneimine800 (PEI800)-EpoxyC16 (PEI-C16), PEI12C16, PEI8C16, and PEI4C16 formed nanoparticle-complex comprises nucleic acid vector, shRNA vector, miRNA and RNAi and have a higher efficiency of nucleic acid transfection when compared to PEI-nanoparticle complexes.

19. The method of claim 12, further comprising transfecting cells with primary monocytes and macrophages comprising:
    contacting leukocytes, myeloid cells, lymphoid cells, monocytes, macrophages and dendritic cells (DC) under conditions in which the cells are transfected in vitro or in vivo with a composition comprising one or more nanoparticles and at least one of a polyethyleneimine800-EpoxyC8-22, an amphiphilic polyethyleneimine800 (PEI800)-EpoxyC16 (PEI-C16), PEI12C16, PEI8C16, or PEI4C16 lipids, complexed with one or more nucleic acid vectors, shRNA vectors, miRNAs, DNA, plasmid DNA, or RNA, on the nanoparticle-lipid complexes.

20. A method of making an amphiphilic polyethyleneimine800 (PEI800)-EpoxyC16 (PEI-C16), PEI12C16, PEI8C16, and PEI4C16 lipid-nanoparticle complex comprising:
    mixing a low molecular weight polyethyleneimine800-EpoxyC8-22, polyethyleneimine800 (PEI800)-EpoxyC16, PEI12C16, PEI8C16, and PEI4C16 with one or more lipids under conditions in which the PEI reacts with the lipids to form amphiphilic PEI lipids; and
    mixing the amphiphilic PEI lipids with nanoparticles under conditions in which the PEI lipids form liposomes and attach to the nanoparticles to form amphiphilic polyethyleneimine800-EpoxyC8-22, polyethyleneimine800 (PEI800)-EpoxyC16 (PEI-C16), PEI12C16, PEI8C16, and PEI4C16 lipid-nanoparticle complexes.

* * * * *